(12) United States Patent
Ehnes et al.

(10) Patent No.: US 12,016,768 B2
(45) Date of Patent: Jun. 25, 2024

(54) STENT-GRAFT WITH IMPROVED FLEXIBILITY

(71) Applicant: TriVascular, Inc., Santa Rosa, CA (US)

(72) Inventors: Dale L. Ehnes, Santa Rosa, CA (US);
Riley King, Santa Rosa, CA (US);
Irma Tapia, Santa Rosa, CA (US);
Chris Staudenmayer, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 0 days.

(21) Appl. No.: 17/695,681

(22) Filed: Mar. 15, 2022

(65) Prior Publication Data

US 2022/0273416 A1  Sep. 1, 2022

Related U.S. Application Data

(63) Continuation of application No. 15/568,834, filed as application No. PCT/US2016/031728 on May 11, 2016, now abandoned.
(Continued)

(51) Int. Cl.
*A61F 2/07* (2013.01)
*A61F 2/88* (2006.01)
*A61F 2/89* (2013.01)

(52) U.S. Cl.
CPC .......... *A61F 2/07* (2013.01); *A61F 2002/075* (2013.01); *A61F 2/88* (2013.01); *A61F 2/89* (2013.01); *A61F 2210/0076* (2013.01); *A61F 2220/005* (2013.01); *A61F 2220/0058* (2013.01); *A61F 2230/0067* (2013.01)

(58) Field of Classification Search
CPC ...... A61F 2/07; A61F 2/88; A61F 2/89; A61F 2002/075; A61F 2210/0076; A61F 2220/005; A61F 2220/0058; A61F 2230/0067

See application file for complete search history.

(56) References Cited

U.S. PATENT DOCUMENTS 5,476,506 A   12/1995  Lunn
5,824,040 A   10/1998  Cox et al.
(Continued)

FOREIGN PATENT DOCUMENTS

EP   1360967 B1   6/2013
JP   2002-501404 A   1/2002
(Continued)

OTHER PUBLICATIONS

PCT Written Opinion dated Oct. 14, 2016.
(Continued)

*Primary Examiner* — Brian A Dukert
*Assistant Examiner* — Rebecca Lynee Zimmerman
(74) *Attorney, Agent, or Firm* — Foley & Lardner LLP

(57) ABSTRACT

A flexible stent-graft has polymeric, non-textile graft layers with a stent disposed between or among the graft layers while allowing for movement of the stent between or among the layers. The stent includes an undulating wire stent disposed within pockets of non-secured graft portions between graft layers. The stent may be a ribbon stent having a ribbon or ribbons of graft layers.

20 Claims, 18 Drawing Sheets

Related U.S. Application Data

(60) Provisional application No. 62/159,415, filed on May 11, 2015.

(56) References Cited

U.S. PATENT DOCUMENTS

| | | | |
|---|---|---|---|
| 6,224,625 | B1 | 5/2001 | Jayaraman |
| 6,264,684 | B1 | 7/2001 | Banas et al. |
| 6,361,637 | B2 | 3/2002 | Martin et al. |
| 6,364,904 | B1 | 4/2002 | Smith |
| 6,395,019 | B2 | 5/2002 | Chobotov |
| 6,398,803 | B1 | 6/2002 | Layne et al. |
| 6,673,103 | B1 | 1/2004 | Golds et al. |
| 6,776,604 | B1 | 8/2004 | Chobotov et al. |
| 6,866,805 | B2 | 3/2005 | Hong et al. |
| 7,081,129 | B2 | 7/2006 | Chobotov |
| 7,090,693 | B1 | 8/2006 | Chobotov et al. |
| 7,125,646 | B2 | 10/2006 | Chobotov et al. |
| 7,147,455 | B2 | 12/2006 | Chobotov et al. |
| 7,147,660 | B2 | 12/2006 | Chobotov et al. |
| 7,147,661 | B2 | 12/2006 | Chobotov et al. |
| 7,150,758 | B2 | 12/2006 | Kari et al. |
| 7,163,553 | B2 | 1/2007 | Limon |
| 7,267,685 | B2 | 9/2007 | Butaric et al. |
| 7,294,147 | B2 | 11/2007 | Hartley |
| 7,615,071 | B2 | 11/2009 | Chobotov |
| 7,678,217 | B2 | 3/2010 | Chobotov et al. |
| 7,682,475 | B2 | 3/2010 | Chobotov et al. |
| 7,686,842 | B2 | 3/2010 | Pavcnik et al. |
| 7,766,954 | B2 | 8/2010 | Chobotov et al. |
| 8,025,693 | B2 | 9/2011 | Quigley |
| 8,062,346 | B2 | 11/2011 | Quigley et al. |
| 8,167,927 | B2 | 5/2012 | Chobotov |
| 8,728,372 | B2 | 5/2014 | Humphrey et al. |
| 8,784,477 | B2 | 7/2014 | Bregulla et al. |
| 9,060,852 | B2 | 6/2015 | Grewe et al. |
| 9,066,828 | B2 | 6/2015 | Geusen et al. |
| 9,132,025 | B2 | 9/2015 | Aristizabal et al. |
| 9,233,015 | B2 | 1/2016 | Geusen et al. |
| 2002/0178570 | A1 | 12/2002 | Sogard et al. |
| 2003/0216805 | A1 | 11/2003 | Edwin et al. |
| 2004/0122508 | A1* | 6/2004 | White .................. A61F 2/07 |
| | | | 623/1.33 |
| 2005/0222667 | A1* | 10/2005 | Hunt .................... A61F 2/07 |
| | | | 623/1.13 |
| 2006/0036311 | A1 | 2/2006 | Nakayama et al. |
| 2007/0208421 | A1 | 9/2007 | Quigley |
| 2007/0219622 | A1* | 9/2007 | Kuppurathanam ....... A61F 2/07 |
| | | | 623/1.13 |
| 2008/0119924 | A1 | 5/2008 | Thistle |
| 2008/0119943 | A1* | 5/2008 | Armstrong ............. A61F 2/89 |
| | | | 623/23.7 |
| 2008/0208319 | A1 | 8/2008 | Rabkin et al. |
| 2009/0030499 | A1* | 1/2009 | Bebb ..................... A61F 2/07 |
| | | | 623/1.13 |
| 2009/0099649 | A1 | 4/2009 | Chobotov et al. |
| 2010/0016945 | A1 | 1/2010 | Bogert et al. |
| 2010/0286760 | A1 | 11/2010 | Beach et al. |
| 2011/0087319 | A1* | 4/2011 | Hagaman ............... A61F 2/07 |
| | | | 156/252 |
| 2012/0330402 | A1* | 12/2012 | Vad ..................... A61F 2/88 |
| | | | 623/1.13 |
| 2013/0085565 | A1 | 4/2013 | Eller et al. |
| 2013/0261734 | A1 | 10/2013 | Young et al. |
| 2015/0088244 | A1 | 3/2015 | Chobotov |

FOREIGN PATENT DOCUMENTS

| | | |
|---|---|---|
| WO | WO-98/31305 A1 | 7/1998 |
| WO | WO-01/06953 A1 | 2/2001 |
| WO | WO-2004/022150 A1 | 3/2004 |
| WO | WO-2012/088475 A1 | 6/2012 |

OTHER PUBLICATIONS

Chinese Office Action dated Jan. 3, 2023, for application No. 202010041724.6.
Chinese Office Action dated Dec. 14, 2018, from application No. 201680027397.0.
Chinese Office Action dated Jan. 6, 2022, from application No. 202010041724.6.
Chinese Office Action dated May 31, 2019, from application No. 201680027397.0.
Extended European Search Report dated Dec. 3, 2018, from application No. 16793394.4.
Japanese Office Action dated Apr. 13, 2020, from application No. 2017-558714.
Japanese Office Action dated Feb. 21, 2022, from application No. 2021-046156.
U.S. Final Office Action dated Feb. 19, 2021, from U.S. Appl. No. 15/568,834.
U.S. Final Office Action dated Sep. 30, 2019, from U.S. Appl. No. 15/568,834.
U.S. Non-Final Office Action dated Jan. 30, 2019, from U.S. Appl. No. 15/568,834.
U.S. Non-Final Office Action dated May 15, 2020, from U.S. Appl. No. 15/568,834.
U.S. Non-Final Office Action dated Sep. 16, 2021, from U.S. Appl. No. 15/568,834.
Chinese Office Action dated Aug. 15, 2023, for application No. 202010041724.6, 19 pages.
Chinese Office Action dated Nov. 16, 2023, for application No. 202010041724.6.

* cited by examiner

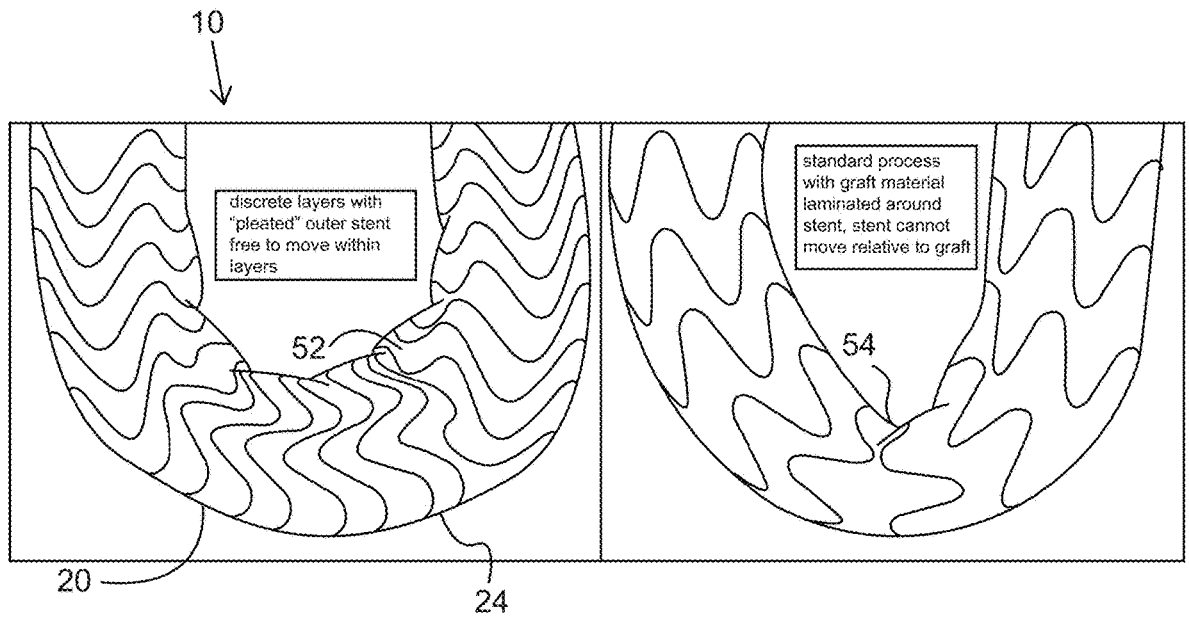
FIG. 20
FIG. 21
(Prior Art)
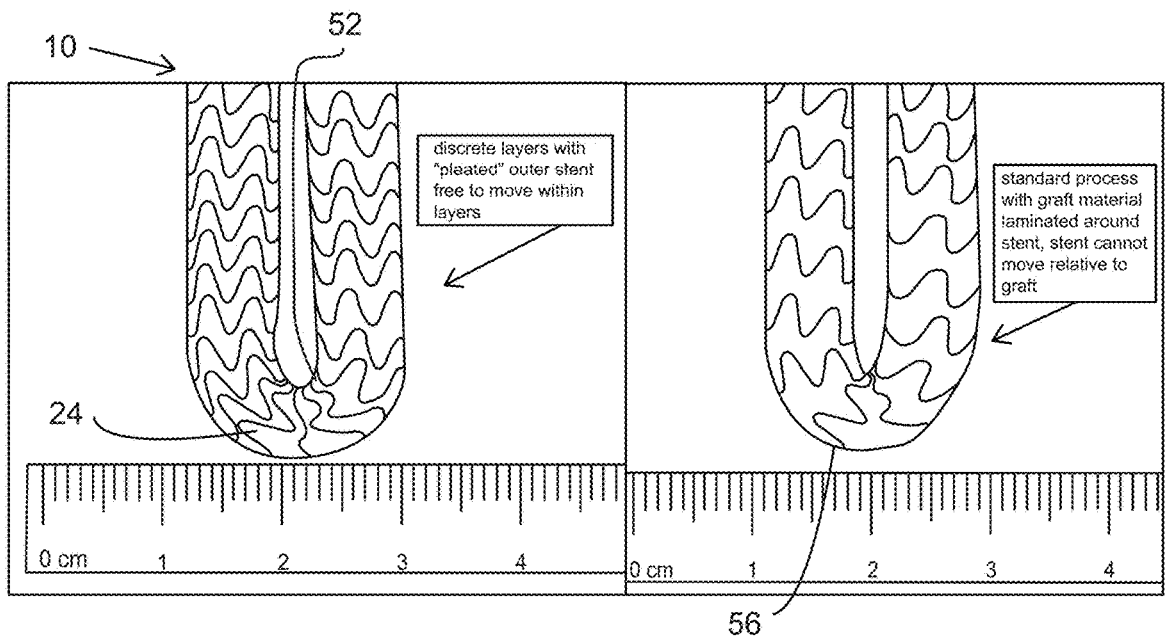
FIG. 22
FIG. 23
(Prior Art)

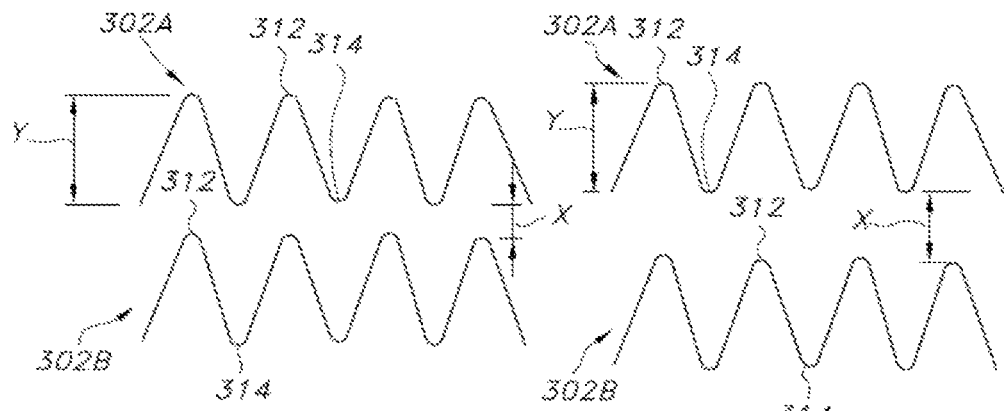
FIG. 33A
FIG. 33B
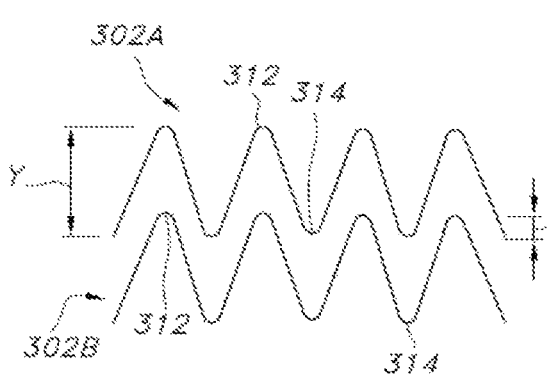
FIG. 33C
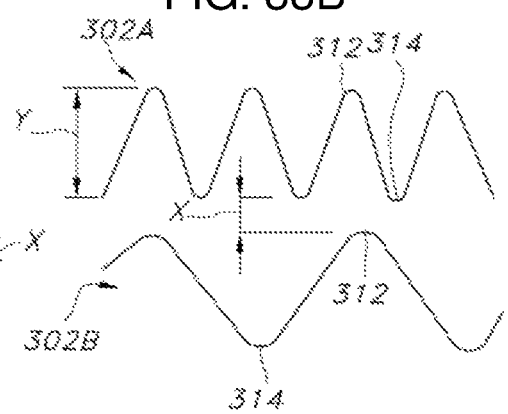
FIG. 33D
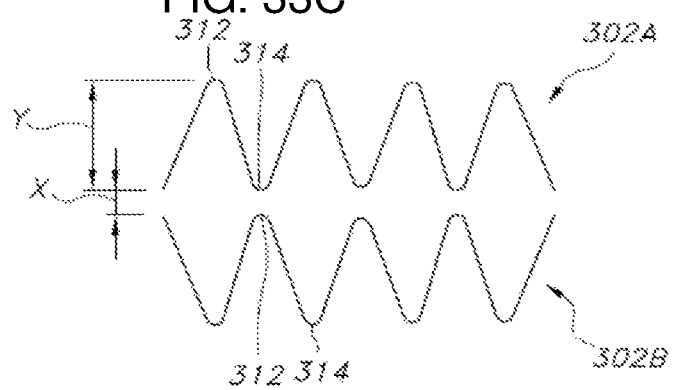
FIG. 33E

STENT-GRAFT WITH IMPROVED FLEXIBILITY

CROSS-REFERENCE TO RELATED APPLICATIONS

This application is a continuation of U.S. Non-provisional application Ser. No. 15/568,834, filed Oct. 24, 2017, which is a national stage application under 35 U.S.C. § 371 claiming the benefit of International Patent Application No. PCT/US2016/031728, filed May 11, 2016, which claims the benefit of U.S. Provisional Application No. 62/159,415, filed May 11, 2015, the contents of each of which are incorporated by reference herein in its their entireties.

FIELD OF THE INVENTION

The present technology is directed to stent-grafts. In particular, the present technology is directed to flexible stent-grafts having polymeric, non-textile graft layers with a stent disposed between or among the graft layers while allowing for movement of the stent between or among the layers.

BACKGROUND OF THE INVENTION

A stent-graft may include a stent associated with one or more textile graft layers. As used herein a textile graft layer refers to a layer formed by typical textile processes, such as weaving, knitting, braiding and the like. The stent is typically secured to the graft layer(s) through the use of sutures. A disadvantage of such textile-containing stent-grafts is high profile, i.e., relatively thick textile layers, especially where the stent-graft is to be fluid tight, for example to limit, prevent or otherwise control blood flow through some or all of the textile walls of a graft layer or layer.

To reduce the profile of a stent-graft, polymeric, non-textile layers may be used. As used herein, a polymeric, non-textile layer refers to sheet or cylinder of polymeric material, such as but not limited to extruded polymeric sheets and cylinders. Typically, such a stent-graft may be fabricated on a cylindrical mandrel, where the graft is laminated in a purely cylindrical form which limits the motion of the stent-graft when it is trying to accommodate longitudinal compression. The ability for a stent-graft to be longitudinally compressed, however, is useful so that the stent-graft can bend and be more readily conform to particular anatomies as well facilitate introduction or delivery procedures. However, shear forces often exist in certain stent-grafts that limit the amount of flexibility when they are manufactured in a purely cylindrical form. This is particularly true when the top or outer and the bottom or inner layers are fully fused together in forming a stent-graft.

Thus, there is a need for a flexible stent-graft having one or more polymeric, non-textile graft layers with a stent disposed between or among the graft layers.

SUMMARY OF THE INVENTION

The present inventive technology provides a low profile flexible stent-graft having polymeric, non-textile graft layers with a stent disposed between or among the graft layers. One or more of the non-textile graft layers may be processed to have increased flexibility between the zigzags or open latticework of the stent. Furthermore, a stent-graft of the present technology may contain areas where the inner and outer graft layers are not laminated to one and the other, thereby allowing stent portions to move or float among such open pockets of graft materials. In some embodiments significant portion of the stent may be free-floating between graft layers. Other methods and embodiments are described for removing or reducing constraints, thereby allowing the stent to be free floating to various degrees, e.g., totally, substantially, significantly or partially within the graft materials.

In one embodiment, an endovascular stent-graft comprises a tubular stent wall having opposed first and second ends; an undulating wire having a thickness and having opposed first and second ends and being helically wound into a plurality of approximate circumferential windings to define the stent wall; the undulating wire having a plurality undulations defined by peaks and valleys with peaks of adjacent approximate circumferential windings being separated by a distance; the first wire end secured to a first undulation at the first end; the second wire end secured to a second undulation at the second end; a graft liner comprising a layer of non-textile, polymeric graft material; and a graft cover comprising a layer of non-textile, polymeric graft material. The graft liner and the graft cover may be selectively secured to each other defining secured graft portions thereat and defining non-secured graft portions therein between, with the non-secured graft portions defining a graft cavity between the graft liner and the graft cover. The tubular stent wall is disposed within the graft cavity. The graft cavity may have a longitudinal extent greater than the thickness of the undulating wire.

In another embodiment, an endovascular stent-graft comprises a tubular stent wall having opposed first and second ends; an undulating wire having a thickness and having opposed first and second ends and being helically wound into a plurality of approximate circumferential windings to define the stent wall; the undulating wire having a plurality undulations defined by peaks and valleys with peaks of adjacent approximate circumferential windings being separated by a distance; the first wire end secured to a first undulation at the first end; the second wire end secured to a second undulation at the second end; a graft liner having opposed first and second end portions and a medial portion therein between, the graft liner comprising a layer of non-textile, polymeric graft material; and a graft cover having opposed first and second end portions and a medial portion therein between, the graft liner comprising a layer of non-textile, polymeric graft material; wherein the first end portion of the graft liner and the first end portion of the graft cover are secured to each other; wherein the second end portion of the graft liner and the second end portion of the graft cover are secured to each other; wherein at least one portion of the medial portions of the graft cover and the graft liner are not secured to each other defining a non-secured graft portion thereat, the non-secured graft portion defining a graft cavity between the graft liner and the graft cover; and wherein the tubular stent wall is disposed within the graft cavity.

In yet another embodiment, an endovascular stent-graft comprises a ribbon stent-graft; comprising a tubular stent wall having opposed first and second ends; an undulating wire having a thickness and having opposed first and second ends and being helically wound into a plurality of approximate circumferential windings to define the stent wall; the undulating wire having a plurality undulations defined by peaks and valleys with medial wire portions coextensive with the peaks and valleys, wherein the peaks of adjacent approximate circumferential windings are separated by a distance; the first wire end secured to a first undulation at the first end; the second wire end secured to a second undulation at the second end; an elongate planar ribbon liner having opposed first and second end portions and a medial portion therein between, the planar ribbon liner comprising a layer of non-textile, polymeric graft material; and an elongate planar ribbon cover having opposed first and second end portions and a medial portion therein between, the planar ribbon liner comprising a layer of non-textile, polymeric graft material; wherein the elongate ribbon cover is disposed over the medial wire portions; wherein the elongate ribbon liner is disposed under the medial wire portions; wherein the elongate ribbon cover and the elongate ribbon liner are securably disposed to each other and to the medial wire portions. The endovascular stent-graft may further comprise a tubular graft liner having opposed first and second end portions and a medial portion therein between, the graft liner comprising a layer of non-textile, polymeric graft material; and a tubular graft cover having opposed first and second end portions and a medial portion therein between, the graft liner comprising a layer of non-textile, polymeric graft material; wherein the first end portion of the tubular graft liner and the first end portion of the tubular graft cover are secured to each other; wherein the second end portion of the tubular graft liner and the second end portion of the tubular graft cover are secured to each other; wherein at least one portion of the medial portions of the tubular graft cover and the tubular graft liner are not secured to each other defining a non-secured tubular graft portion thereat, the non-secured tubular graft portion defining a graft cavity between the tubular graft liner and the tubular graft cover; and wherein the ribbon stent-graft is disposed within the graft cavity.

These features of embodiments will become more apparent from the following detailed description when taken in conjunction with the accompanying exemplary drawings. Corresponding reference element numbers or characters indicate corresponding parts throughout the several views of the drawings.

BRIEF DESCRIPTION OF THE DRAWINGS

FIG. 20 depicts bending of the stent-graft according to the present inventive technology where stent wire elements are movable near the bend and where graft portion form crimps near the bend.

FIG. 21 depicts bending of a stent-graft of the prior art.

FIG. 22 depicts increased bending of the stent-graft of FIG. 20.

FIG. 23 depicts increased bending of the prior art stent-graft of FIG. 21.

FIGS. 33A through 33E depict various arrangements of helically wound stents of the present inventive technology.

DETAILED DESCRIPTION OF THE INVENTION

With regard to graft, stent or stent-graft embodiments discussed herein and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
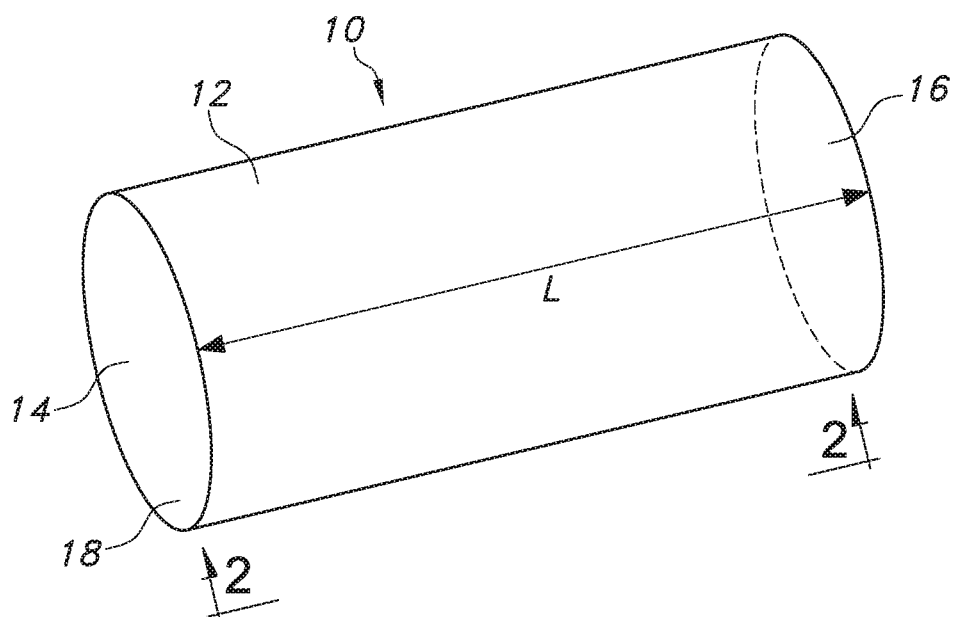
FIG. 1 is a perspective and schematic view of a stent-graft according to the present inventive technology.

FIG. 1 is a schematic and perspective view of a stent-graft 10 according to the present inventive technology. The stent-graft 10 is a hollow tubular device having a tubular wall 12 having a longitudinal length L or axis L, a first open end 14 and an opposed second open end 16 to define an open lumen 18. While the stent-graft 10 in FIG. 1 is depicted as being substantially tubular, the present inventive technology is not so limited. For example, portions of the stent-graft wall 12 at either or both of the open ends 14, 16 may be flared (inwardly or outwardly) or flanged (inwardly or outwardly). Furthermore, portions of the stent-graft wall 12 between the open ends 14, 16 may also have non-straight tubular portions, such as flared (inwardly or outwardly) portions or portion having bends of curvature along portions of the stent-graft wall 12. Moreover, while the open ends 14, 16 are depicted has having a single open lumen 18, the present inventive technology is not so limited. For example, one or both ends 14, 16 may be multi-lumen ends, such as but not limited to bifurcated open ends.

Moreover, the present inventive technology is not limited to a continuous tubular wall 12 as depicted in FIG. 1. For example, the stent-graft 10 may have one or more fenestrations (not shown) in the tubular wall 12. Such fenestrations may be useful in branched lumens where additional stent-grafts may be deployed at branched lumens and into the fenestrations. Furthermore, the stent-graft 10 may have one or more side branches (not shown) extending from medial portions of the tubular wall 12 for deployment into or towards branched lumens.

Figure 2:
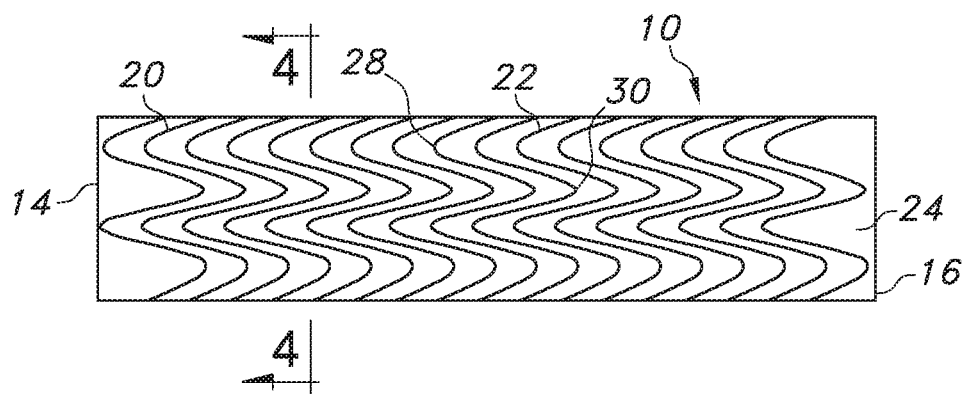
FIG. 2 is a side elevational view the stent-graft of FIG. 1 taken along the 2-2 axis depicting a stent according to the present inventive technology.
Figures 34A, 34B:
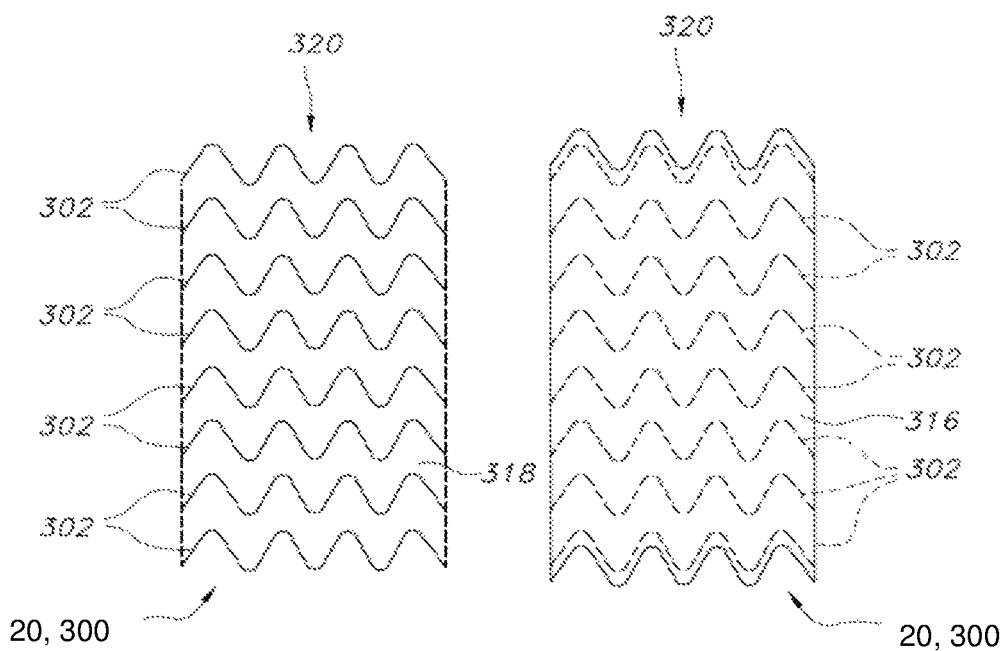
FIGS. 34A and 34B depict stent-graft assemblies useful in the present inventive technology.

FIG. 2 is a side elevational view of the stent-graft 10 of FIG. 1 taken along the 2-2 axis. The stent-graft 10 includes a stent 20 formed from an undulating wire 22. The undulating wire 22 may be helically wound, or otherwise formed, into the stent 20 having a series of peaks 28 and valleys 30. Further details of the stent 20 are described below in conjunction with FIGS. 31, 32A-32B, 33A-33E and 34A-34B. The stent-graft 10 includes a graft cover 24. A graft liner 26 (not shown) is disposed underneath the graft cover 24. Further details of the graft cover 24 and the graft liner 26 and the graft liner are described below in conjunction with FIGS. 34A and 34B. The graft cover 24 and the graft liner 26 may be one or more layers of polymeric materials.

Figure 3:
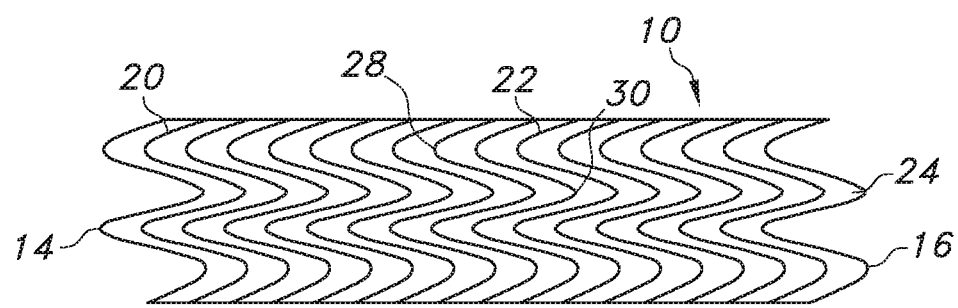
FIG. 3 is a side elevational view of the stent-graft of FIG. 2 having graft material trimmed from the ends of the stent-graft.

The graft cover 24 (and the graft liner 26—not shown) may extend to first and second ends 14, 16 of the stent-graft 10. As depicted in FIG. 2, the stent-graft 10 may have graft cover and graft liner materials extending beyond the terminal portions of the undulating wire at the first and second ends 14, 16. Such a configuration may be useful where, for example, additional area for fusing other graft components at the first and second ends 14, 16 is desired. The present inventive technology, however, is not so limited. For example, as depicted in FIG. 3, an embodiment of the stent-graft 10 may have the graft cover 24 (and the graft liner 26—not shown) trimmed from the first and second ends 14, 16 or otherwise not present.

Figure 4:
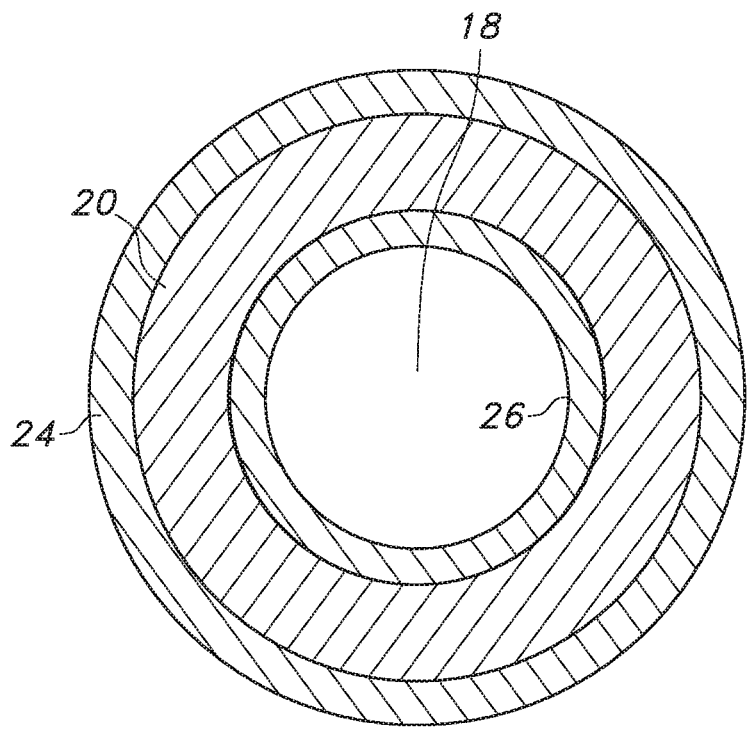
FIG. 4 is a cross-sectional view the stent-graft of FIG. 2 taken along the 4-4 axis.

FIG. 4 is a cross-sectional view of the stent-graft 10 of FIG. 1 taken along the 4-4 axis. As depicted in FIG. 2, the stent 20 is disposed between the graft cover 24 and the graft liner 24. Unlike typical prior art stent-grafts, the stent 20 or portions of the stent 20 of the present technology are free to move or float between the graft cover 24 and the graft liner 26. Such free movement or floating permits, among other things, greater flexibility of the stent-graft 10 of the present inventive technology during assembly as well as during and after deployment as compared to stent-grafts of the prior art.

Figure 5:
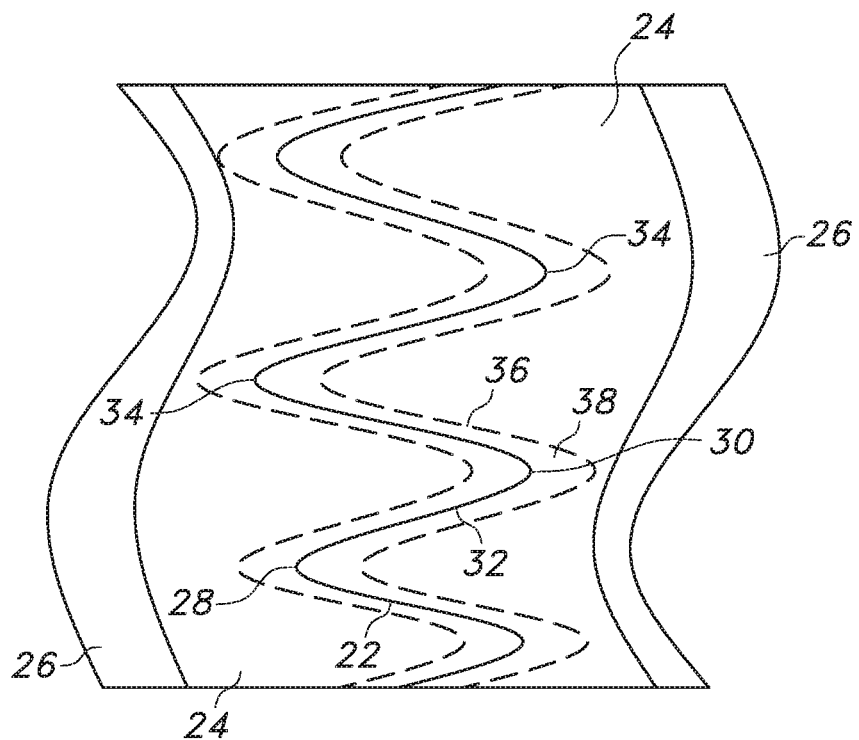
FIG. 5 is a partial side elevational view of the stent-graft according to the present inventive technology showing a portion of an undulating wire stent disposed within graft cavities or non-secured graft portions defined by graft secured portions.

FIG. 5 is a partial side elevational view of the stent-graft 10 of FIG. 1 showing a portion of an undulating wire 22 disposed within graft cavities 38 or non-secured graft portions 38. The undulating wire 22 is disposed between the graft cover 24 and the graft liner 26. Secured graft portions 36 may be formed about both sides of the undulating wire 22. As depicted in FIG. 5, peaks 28, valleys 30 and medial portion 32 of the undulating wire 22 may be disposed within the graft cavities 38 or the non-secured graft portions 38. Terminal portions of the peaks 28 and/or valleys 30 may be referred to as crown portions 34, which will be described in further detail below. Although FIG. 5 depicts entire portions of the peaks 28, valleys 30, crown portions 34 and medial portions 32 of the undulation wire 22 as being disposed within the graft cavities 38 or the non-secured graft portions 38, the present inventive technology is not so limited. For example only portions of the peaks 28, valleys 30, crown portions 34 and/or medial portions 32 of the undulation wire 22 may be disposed within the graft cavities 38 or the non-secured graft portions 38.

The secured graft portions 36 may be formed by the application of heat, e.g., lamination, with or without the application of pressure, by adhesive bonding, ultrasonic bonding or any combination thereof. The secured graft portions 36 may be laminated through the selective application of heat, such as through the use of a laser or a heated probe. Furthermore, a tool (not shown) may be disposed underneath the portions 38 while the stent-graft 10 is on a mandrel (not shown) to aid in the formation of the secured graft portions 36. Moreover, an inflation tool (not shown) may be used to provide an inflation medium, such as but not limited to air or other suitable fluid, to inflate areas between the graft cover 24 and the graft liner 26, thereby forming a cavity 38 after selective securement of portion of the graft cover 26 and graft liner 26 to each other. Still furthermore, the present inventive technology is not limited to the formation of graft cavities 38 having the stent 20 or the undulating wire 22 disposed therein. A graft cavity 38, if desired, may be formed within the graft cover 26 and the graft liner 26 at locations not having a portion of the stent 20. Between the undulating wire 22 and the secured graft portions 36 are non-secured graft portions 38 or graft cavity portions 38. Such non-secured graft portions or cavities 38 permit movement of the undulating wire 22 or stent 20 within the stent-graft 10 upon movement of the stent-graft, such as but not limited to bending of the stent-graft 10, axial or longitudinal compression or expansion of the stent-graft 10, radial compression or expansion of the stent-graft 10. Such stent-graft movements are often encountered during deployment of the stent-graft 10 to a desired bodily location or lumen(s) or are even encountered after deployment of the stent-graft 10 with the body.

In an embodiment of the present inventive technology, one method may involve welding or bonding (thermally, ultrasonically, adhesives or other means) a path in between the stent members or zigzags to seal each zigzag pattern within its own pouch or area of non-laminated graft material layers. Sintering/laminating may be done with minimal pressure, for example without compressive force during lamination, such as typically used with shrink or compressible tube, such that the graft layers will not generally fuse together locally around the stent member or wire, thereby leaving it free to have relative motion within the pocket of non-laminated graft layers. Such selective welding may simply leave a weld line path among the stent members or wires. A device with a thermal tip or an ultrasonic horn may suitable be used to form such weld lines. The device could be manually operated or could be automatic, i.e., robotic movement control.

Figure 6:
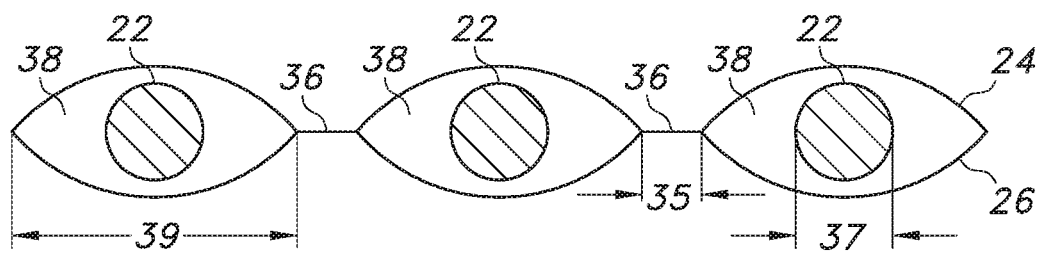
FIG. 6 is a partial cross-sectional view of the stent-graft of FIG. 5.
Figure 7:
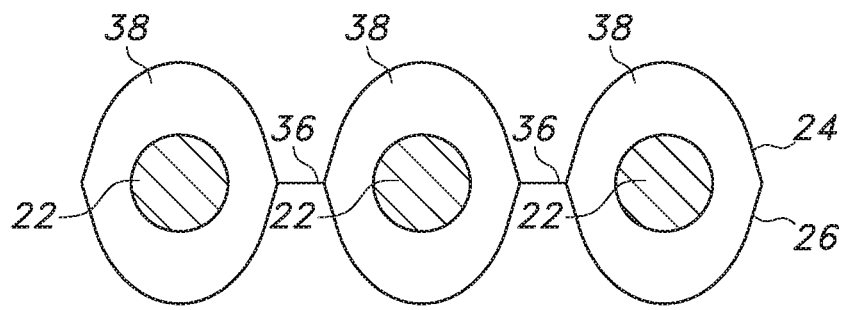
FIG. 7 depicts the stent-graft of FIG. 6 being partially compressed.

FIG. 6 is a partial cross-section view of the stent-graft 10 of FIG. 1. The undulating wire 22 is moveable within the graft cavities 38. For example, as depicted in FIG. 7, when the stent-graft 10 of FIG. 6 is compressed, the undulating wires move freely within the cavities 38. Furthermore, the graft cover 24 and/or the graft liner 26 may also freely move upon compression, as depicted in FIG. 7 (both the graft cover 24 and the graft liner are freely moveable).

As depicted in FIG. 6, the secured graft portions 36 may have a small or minor longitudinal extent 35, such as less or substantially less than a diameter 37 of the undulating wire 22 or such as about the diameter 37 of the undulating wire 22. The longitudinal extent 39 of the unsecured portions or cavities 38 may be greater than the minor longitudinal extent 35 and may be greater than the diameter 37 of the undulating wire. The present inventive technology, however, is not so limited. Major or significant portions of the graft cover 24 and the graft liner 26 may be secured to each other, such as significant or substantial cover and liner portions 24, 26 between adjacent undulating wire portions. Such significant or substantial cover and liner portions 24, 26 forming secured graft portions 36 may be about the size of the diameter of the undulating wire 22 or significantly greater.

In general terms, as the volume or extent of the graft cavities 38 is increased with respect to the undulating wire 22, the flexibility of the stent-graft 10 may also increase. The present inventive technology, however, is not limited to increasing the volume or extents of the graft cavities 38 for increasing flexibility of the stent-graft 10, and other techniques, as described below, such as crimping and/or pleating, may suitably be used.

Figure 8:
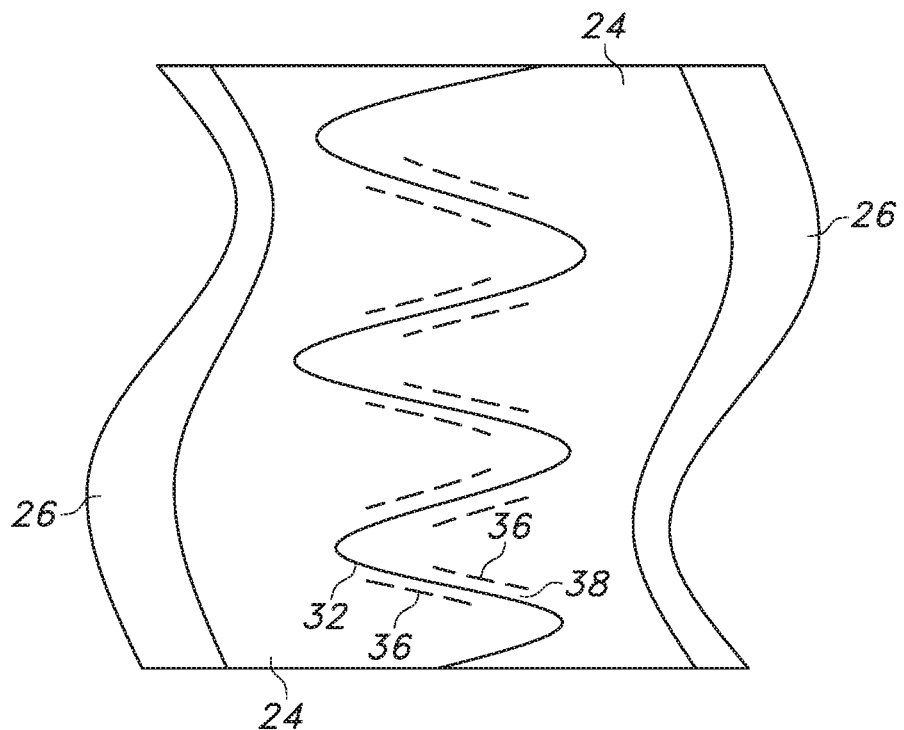
FIGS. 8 to 10 depict the stent-graft of FIG. 5 with various embodiments of graft secured portions.

Moreover, the present inventive technology is not limited to secured graft portions 36 encompassing the undulating wire 22 as depicted in FIG. 5. For example, as depicted in FIG. 8, secured graft portions 36 may be formed at medial portions 32 of the undulating wire 22 between a peak 28 and a valley 30 of the undulating wire. A non-secured graft portion or cavity 38 is formed the secured graft portions 36. Such a configuration permits increased potential for free movement of the peaks 28 and valleys 30 as these peaks 28 and valleys 30 are substantially non-constrained against movement, for example longitudinal movement and/or non-longitudinal movement, such as bending, as compared to stent-grafts having peaks and valleys encapsulated between graft components.

Figure 9:
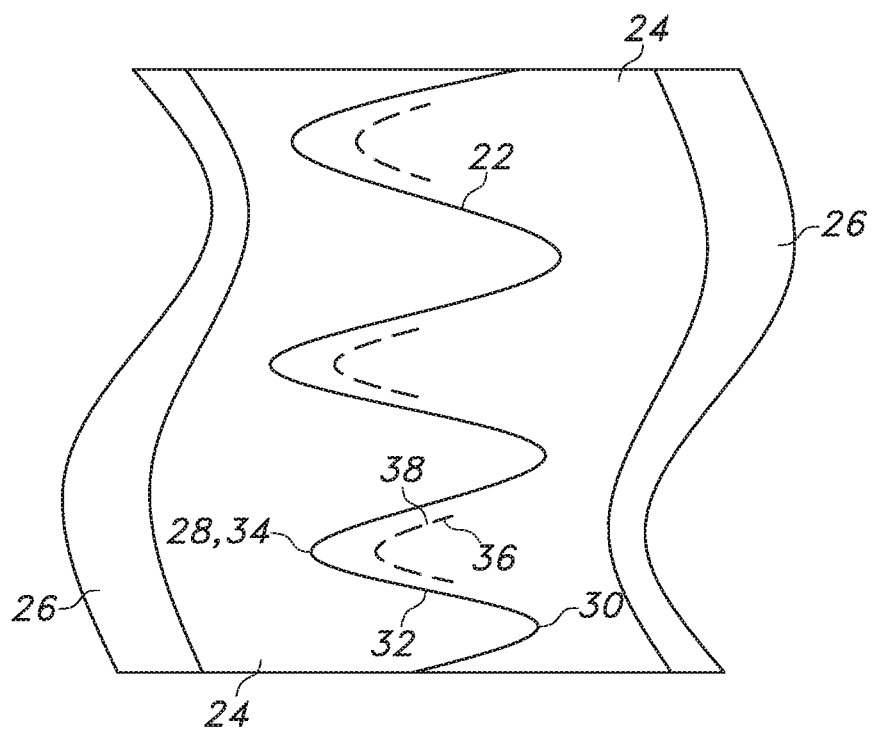

Moreover, as depicted in FIG. 9, secured graft portion 36 may be located at the peaks 28 or crown portion 34 of the undulating wire 22. While the secured graft portions 36 in FIG. 9 are depicted as being only on one side of the peaks 28, the present inventive technology is not so limited. For example, secured graft portions 36 may be disposed on both sides of the peaks 28 (not shown). Additionally, some secured graft portions 36 may be disposed on one side of a peak 28 towards one end of the stent-graft 10, for example the second end 16 of the stent-graft 10, while other secured graft portions 36 may be disposed on the other side of a peak 50 towards another end of the stent-graft 10, for example the first end 14 of the stent-graft 10.

Figure 10:
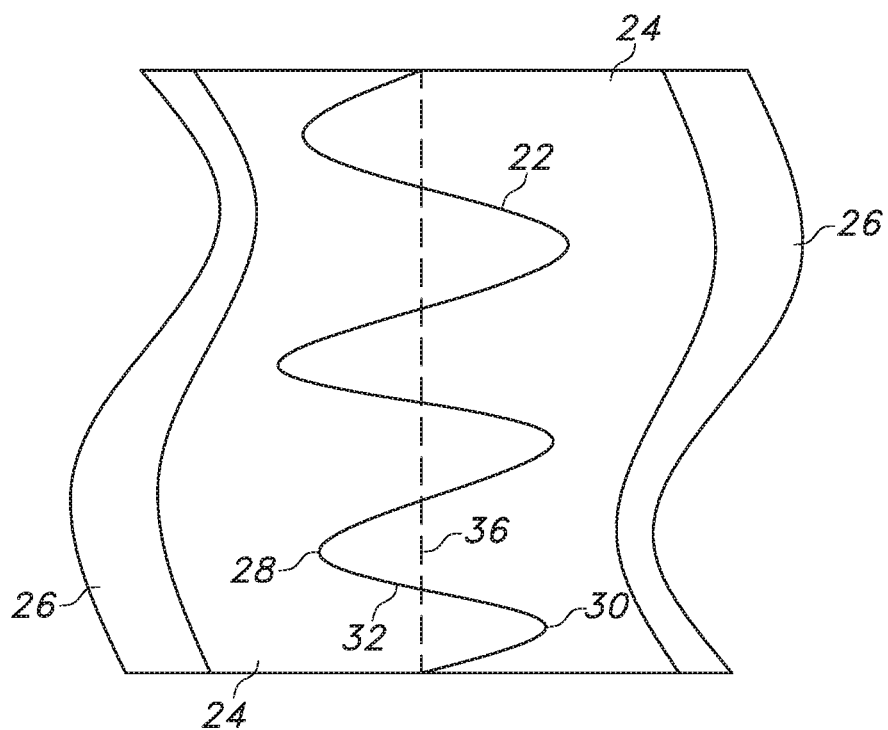

Furthermore, as depicted in FIG. 10, secured graft portions 36 may be formed traversely across portion of the undulating wire 22, such as the medial portion 32 as depicted, or peak portions 28 (not shown) or valley portions 30 (not shown). While the embodiment of FIG. 10 may represent as easier manufacturing technique for forming the secured graft portions 36 as particular geometries of the undulating wire 22 need not be followed precisely, increased stent-graft flexibility is still achieved over prior art stent-grafts having fully encapsulated stents within graft layers.

The various configurations of graft secured portions 36 as depicted in FIGS. 5-10 and described in conjunction with those figures may be used alone or in any combination.

Figure 11:
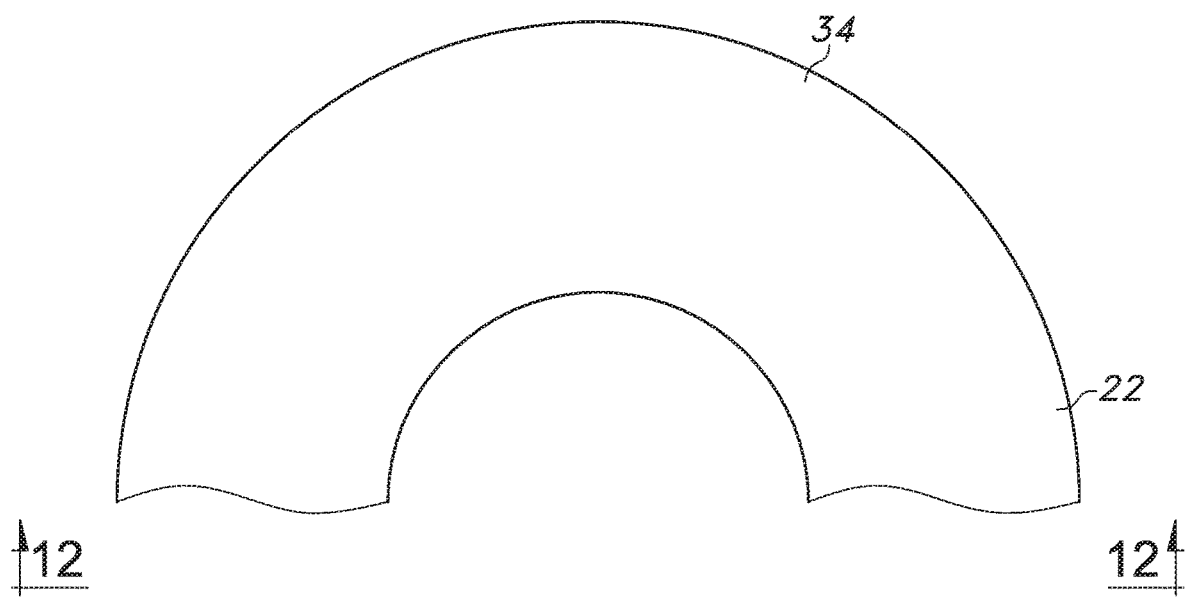
FIG. 11 is a partial view of a stent crown portion of the stent-graft according to the present inventive technology.

FIG. 11 is a top view of a crown portion 34 of the undulating wire 22. FIGS. 12A-12D depict different arrangement of the graft cover 24 and the graft liner 26 about the crown portions 34 of the stent-graft 10 of the present inventive technology.

Figure 12A:
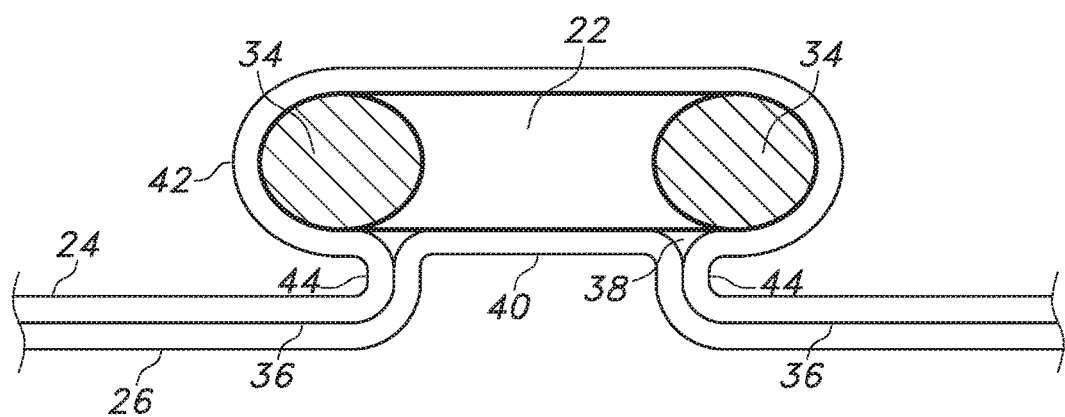
FIGS. 12A to 12D depict various embodiments of graft secured and non-secured portions forming crimps or pleats.

As depicted in FIG. 12A, a graft cover portion 42 of the graft cover 24 may be disposed around a wire portion of the crown portion 34. The graft cover portion 42 is disposed over at least one side of the crown portion 34. Furthermore, the graft cover portion 42 may also be disposed over the top portion of the crown portion 34 and underneath at least a portion of the bottom of the crown portion 34. The graft liner 26 may have a raised graft liner portion 40 underneath a portion of the crown portion 34. While the graft cover 24 and the graft liner 26 are secured to each other at graft secured portions 36, the graft cover 24 and the graft liner 26 may not be completely or directly secured to the crown 34, thereby permitting movement of the crown portion 34 between and along the graft cover 24 and the graft liner 26. For example, if desired, a portion of the graft cover 42 may be laminated to the crown portion 34, as shown in FIG. 12A.

As also depicted in FIG. 12A, graft cover crimp or pleat portions 44 are formed with the raising of the crown portion 34, the graft cover 24 and the graft liner 26 above the longitudinal wall 12 of the stent-graft 10. During fabrication, a tool (not shown) may be used to raise these portions above a mandrel (not shown) for lamination thereat. The crimp or pleat portions 44 provide flexibility at the crowns 34 of the stent-graft 10 during bending and/or compression. As described below, such increased flexibility includes, but is not limited to, increased longitudinal flexibility during longitudinal compression and/or expansion and increased radial flexibility as limited or minor crown movement is permitted in the radial direction upon bending or even longitudinal compression.

Figure 12B:
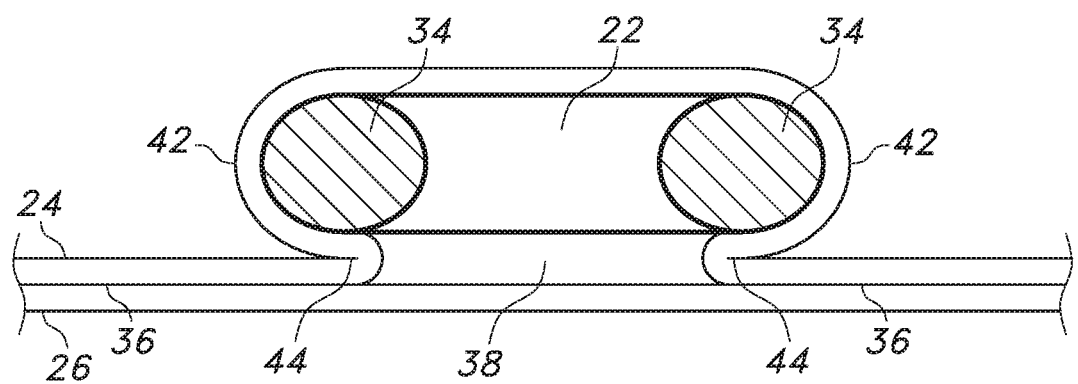

As depicted in FIG. 12B, the present inventive technology need not have a raised liner portion 40. Crimps or pleats 44 may be disposed underneath portion of the crowns 34. The size or extent of the crimps or pleats may vary. The crimps or pleats 44 in FIG. 12B will permit longitudinal flexibility as described above in conjunction with FIG. 12A, but less radial flexibility as the crown portions 34 are not raised as in FIG. 12A.

Figure 12C:
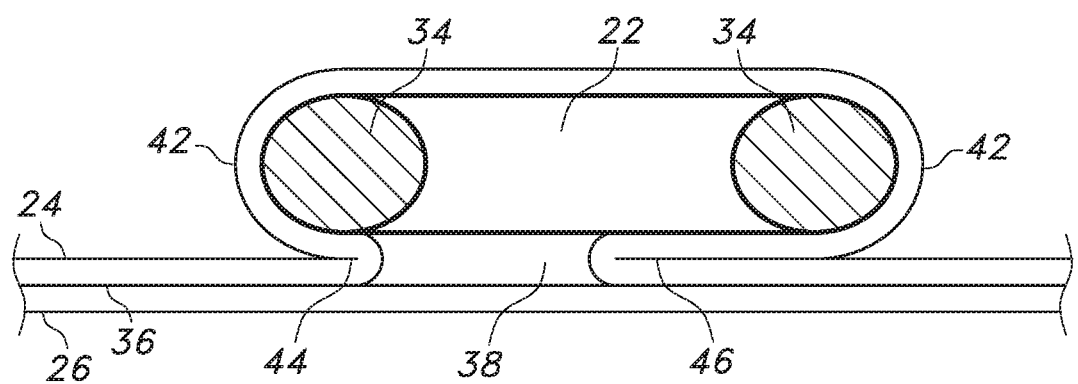

As depicted in FIG. 12C, an elongated graft pleat 46 may be disposed underneath a crown portion, where the extent of the elongated graft pleat 46 is larger than the extent of the crimp or pleat 44. The extent of the crimp or pleat 44 may be from about the diameter of the undulating wire 22 to a fraction, such as half or less, of the diameter of the undulating wire 22. The elongated graft pleat 46 is typically greater than the diameter of the undulating wire 22. In general, increasing extent of the elongated graft pleat 46 increases stent-graft flexibility.

Figure 12D:
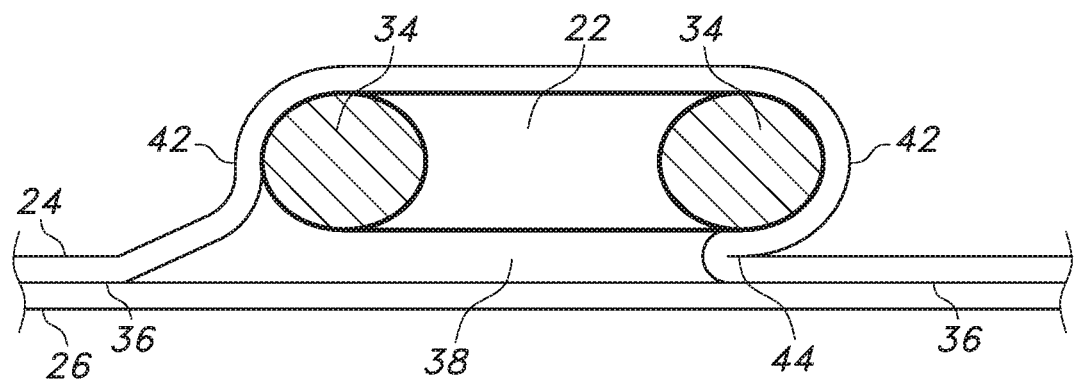

The present inventive technology is not limited to the disposing of crimps or pleats 44, 46 on both sides of the crown portion 34 as depicted in FIGS. 12A-12C. For example, as depicted in FIG. 12D, a crimp or pleat 44 (or pleat 46) may be disposed at only one side of the crown portion 34. In other words, increased stent-graft flexibility may be configured to particular needs and configurations.

FIGS. 13A through 15 depict the stent-graft 10 of the present inventive technology in which stent 20 is substantially disposed between the graft cover 24 and graft liner 26 and within a non-secured graft portion or cavity 38.

Figure 13A:
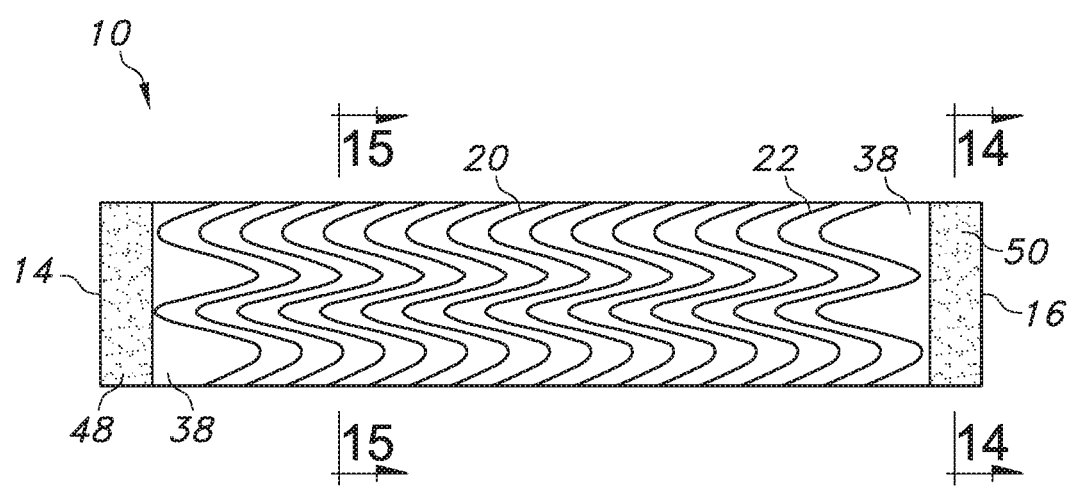
FIG. 13A depicts a stent-graft according to the present inventive technology disposed between a graft cover and a graft liner having the graft ends secured to each other.

As depicted in FIG. 13A, the stent 20 may be disposed between a fused first end 48 and a fused second end 50. Between the two fused graft ends 48, 50 are non-secured graft portion 38 of the graft cover 26 and the graft liner 26. The stent 20 of this embodiment will have increased flexibility within the non-secured graft portion 38 as there is no or substantially no bonding of the undulating wire 22 within the graft cover 24 and the graft liner 26.

Figure 13B:
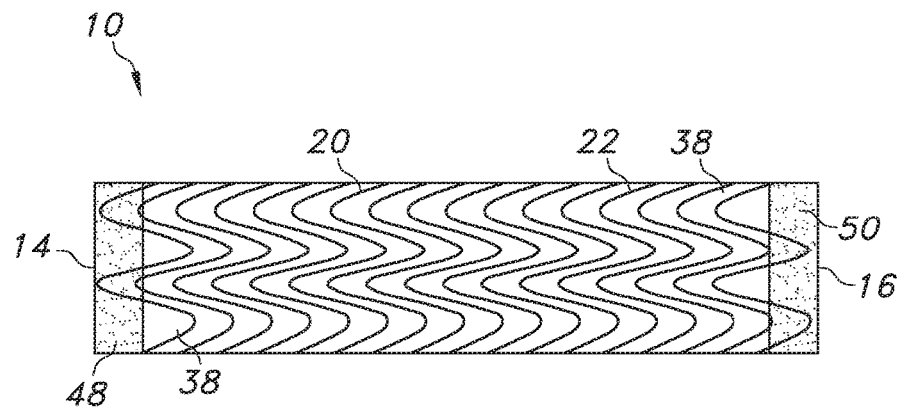
FIG. 13B depicts another embodiment for the stent-graft of FIG. 13A.

While FIG. 13A depicts the stent 20 being entirely between the fused ends, the present inventive technology is not so limited. For example, as depicted in FIG. 13B, portions of the stent 20 may be disposed within the fused ends 48, 50. This embodiment may increase securement of the stent 20 within the stent-graft 10 while still providing improved flexibility of the stent 2 within the stent-graft 10.

Figures 14, 15:
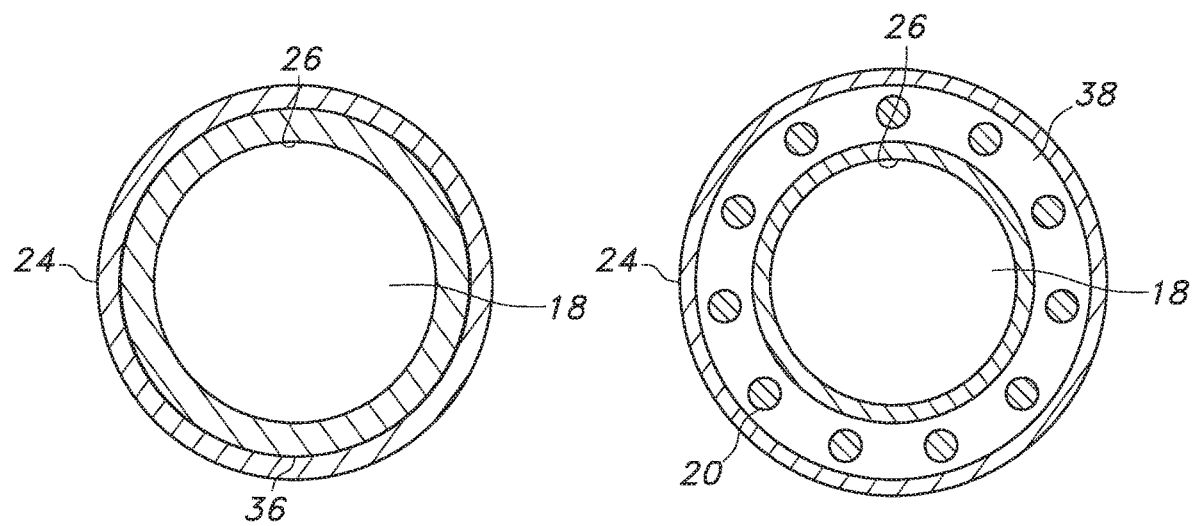
FIG. 14 is a cross-sectional view of the stent-graft of FIG. 13A taken along the 14-14 axis.
FIG. 15 is a cross-sectional view of the stent-graft of FIG. 13A taken along the 15-15 axis.

FIG. 14 is a cross-section view of the stent-graft 10 of FIG. 13A taken along the 14-14 axis. As depicted in FIG. 14, the graft cover 24 and the graft liner 26 are secured to each other, as indicated by secured graft portions 36.

FIG. 15 is a cross-section view of the stent-graft 10 of FIG. 13A taken along the 15-15 axis. As depicted in FIG. 15, the graft cover 24 and the graft liner 26 are not secured to each other, as indicated by the non-secured graft portion or cavity 38. The stent 20 is disposed within the cavity 38, thereby permitting greater movement and flexibility of the stent 20 as compared to prior art stent-grafts.

Figure 16:
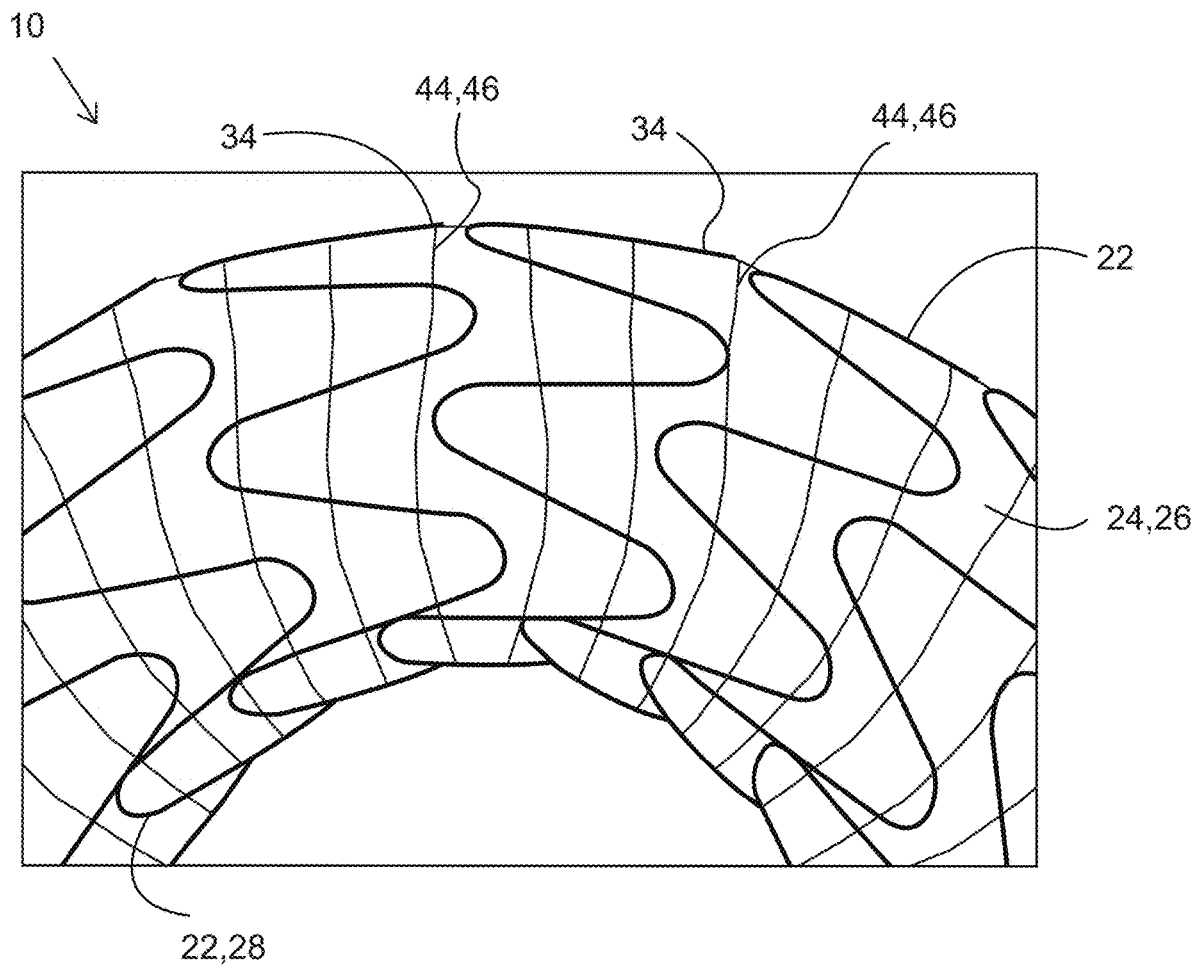
FIG. 16 is a partial, side elevational view of the stent-graft according to the present inventive technology showing stent wire orientations when the stent-graft is bent.

FIG. 16 depicts improved flexibility of an embodiment of the stent-graft 10 while undergoing bending. The crimps or pleats 44, 46 underneath the crown portion 34 permit the crown 34 to partially lift away from the wall of 12 of the stent-graft 10 under the bending force. Moreover, stent undulations become more nested at the bottom portion or inside radius of the bend as shown in FIG. 16, again due to design of the present technology that affords the embodiments the flexibility as described herein. Thus, the stent-graft 10 has enhanced flexibility while still maintaining integrity of the graft cover and liner 24, 26.

Figure 17:
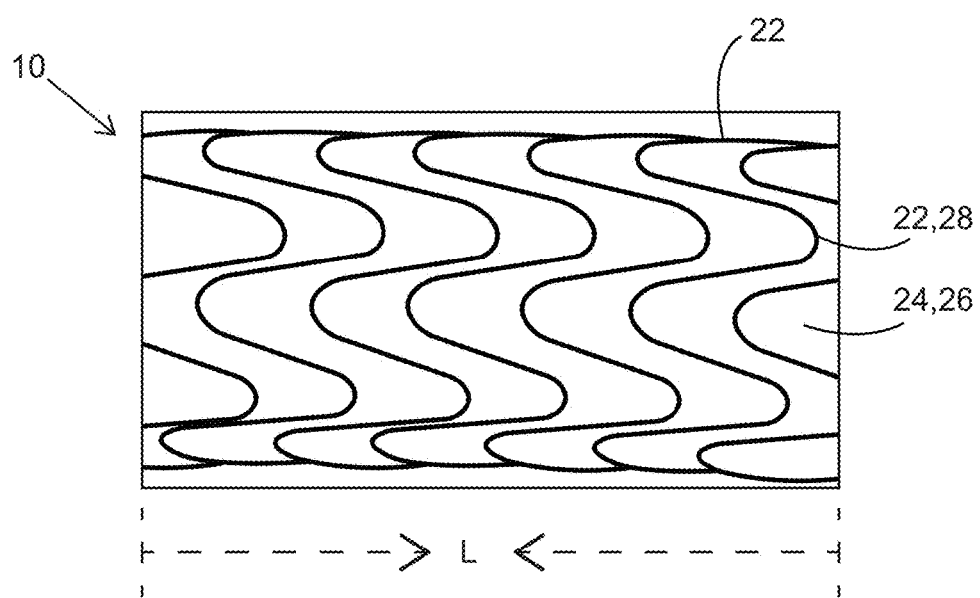
FIG. 17 is a partial, elevational view of the stent-graft according to the present inventive technology showing stent wire orientations when the stent-graft is longitudinally compressed.

As depicted in FIG. 17, increased nesting the stent undulations is also achieved upon axial or longitudinal compression, along the L axis, of the sent-graft 10. The peaks and valleys 28, 30 (respectively) become more nested, or closer together, as the stent-graft 10 is compressed, reflecting the stent-graft's improved flexibility due to, among other things, improved graft cover and liner designs and configurations disclosed herein.

Figure 18A:
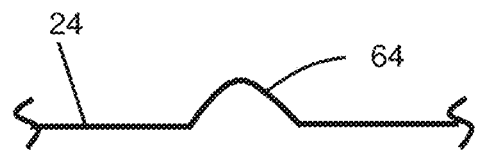
FIGS. 18A through 18D depict graft crimps and graft pleats according to the present inventive technology.
Figure 18B:
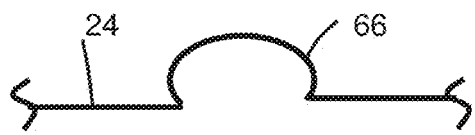
Figure 18C:
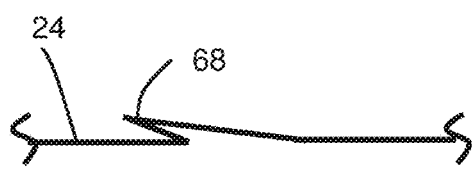
Figure 18D:
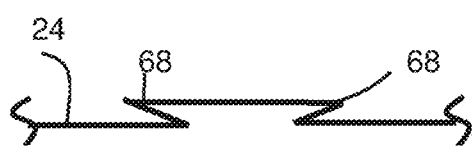

FIGS. 18A-18D depict various crimp and pleat configurations that may be imparted into the graft or which may form in the graft during compression or bending of the stent-graft 10 of the present inventive technology. As depicted in FIG. 13A, a crimp 64 may be a simple protuberance of the graft cover 24, or may be a semi-rounded configuration crimp 66 as depicted in FIG. 18B. As depicted in FIGS. 13C and 13D, pleats 68 may also form or be formed in the graft cover 24. Both crimps 64, 66 and pleats 68 provide improved flexibility in the graft cover 24. The stent-graft 10 may include any combination of crimps 64, 66 and pleats 68. Without limiting the generality of the description of the various embodiments of the present technology, in general as used herein the term "crimp" (e.g., crimps 64, 66) refers to a graft cover or other graft portions or layers that generally form a rounded, semicircular or curvilinear surface when the stent-graft 10 is in a state such as that depicted in FIGS. 18A-18B, while the term "pleat" (e.g., pleats 68) refers to a graft cover or other graft portions or layers that generally form a more angular, creased or folded surface, such as those forming an acute angle, when the stent-graft 10 is in a state such as that depicted in FIGS. 18C-18D. However, it is understood that either term may be used interchangeably when referring to this aspect of the inventive technology."

Figure 19:
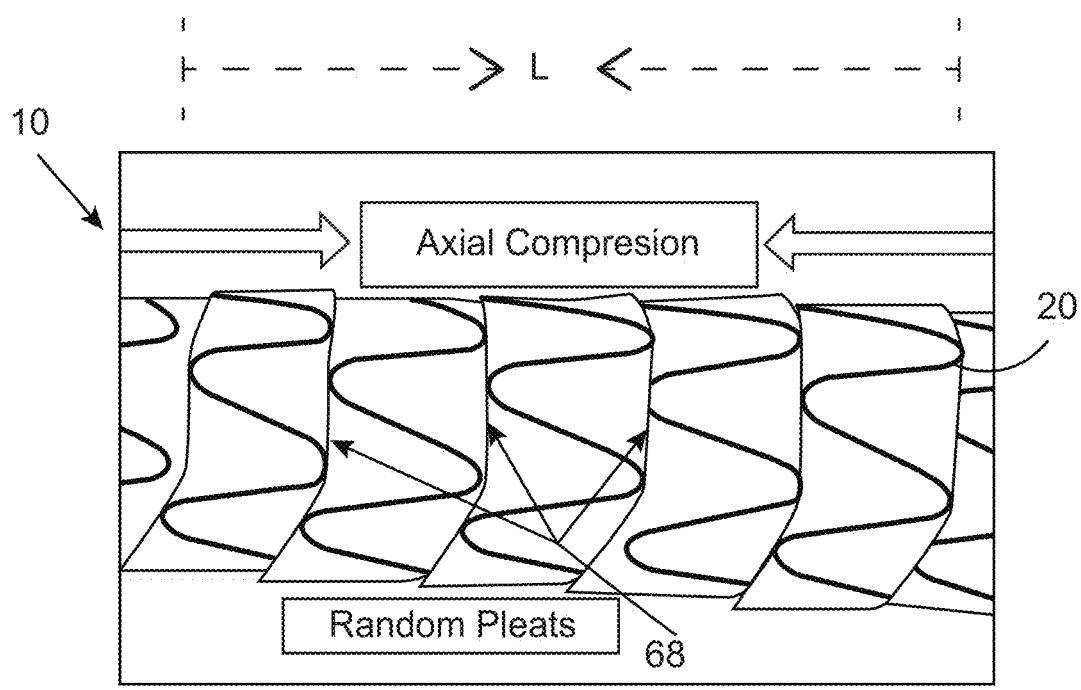
FIG. 19 depicts the formation of graft pleats upon longitudinal compression of the stent-graft according to the present inventive technology.

FIG. 19 depicts the formation of pleats 68 as the stent-graft 10 is axially or longitudinally compressed. The pleats 68 form as the sent-graft 10 is compressed because the flexibility of the device as the graft cover and the graft liner are not fully laminated, sintered or otherwise connected or bonded to each other. Thus, movements of the different portions of the stent 20 are not overly prohibited or restricted by the graft cover or liner 24, 26. Indeed, the formation of pleats 68, as described above, permits movement of the components of the stent-graft 10 where additional graft pleating may be achieved upon longitudinal compression.

FIG. 20 depicts the stent-graft 10 of FIGS. 13A-15 being subject to a bending force. During bending, the pleats of graft cover 24, as indicated by pleats 52, form under the force as the stent 20 is freely moveable within the graft cover 24 and the graft liner 24 through the bent portion. This permits the stent-graft 10 to bend about 180° or greater without the stent-graft 10 having a substantial reduction in diameter in any portion of the bend. Stated another way, the patency of the stent-graft 10, particularly in the area of the bend, and the cross-sectional area of the lumen 18 is maintained during such bending. This results in a higher-performing stent-graft insofar as blood flow is diminished only slightly, or not at all, in clinical applications during and after deployment. In contrast, as depicted in FIG. 21, a stent-graft having a stent disposed between a laminated or sintered graft layers, typical of the prior art, forms a deformed portion 54 while undergoing a similar degree of bending. This deformed portion 54 corresponds to a lumen of reduced patency and less desirable clinical performance FIG. 22 depicts the stent-graft 10 of FIG. 13A being bent to about 180° with about a 6 mm or less gap between portions of the tubular stent-graft 10 in the area of the bend. The stent-graft 10 maintains a substantially tubular shape through the bend; in particular, lumen 18 of the stent-graft 10 in the area of the bend remains patent with little or no reduction in cross-sectional diameter of the stent-graft 10 or lumen 18. In contrast, as depicted in FIG. 23, a stent-graft having a stent disposed between a laminated or sintered graft layers, typical of the prior art, forms a kink 56 and a reduced patency lumen while undergoing a similar degree of bending.

Figure 24:
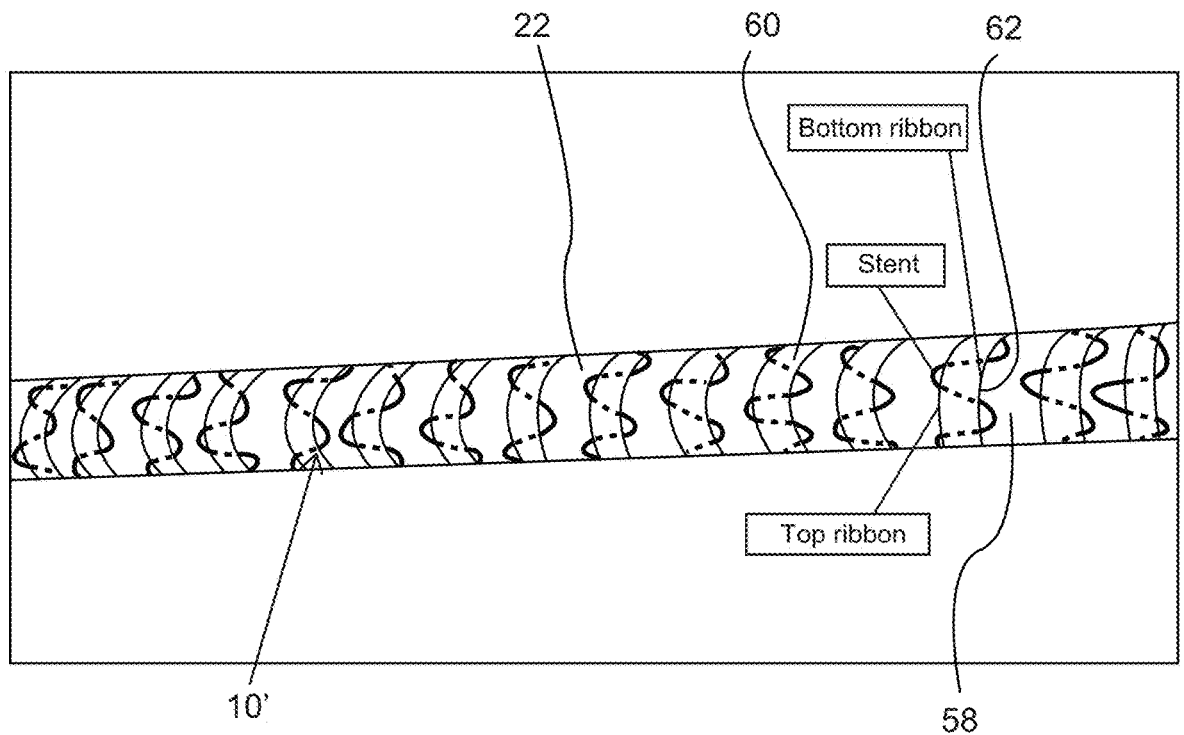
FIG. 24 depicts the forming of a ribbon stent-graft on a mandrel according to the present inventive technology.
Figure 25:
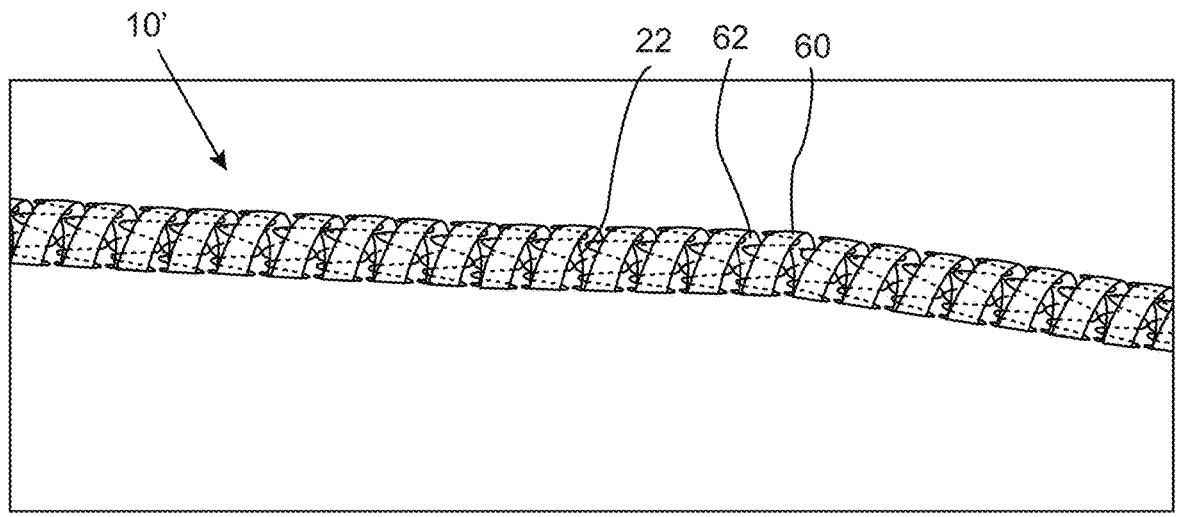
FIGS. 25 and 26 depict the ribbon stent-graft of FIG. 24.

FIG. 24 depicts an embodiment of a ribbon stent-graft 10' according to the present inventive technology. During fabrication, the ribbon stent-graft 10' may be formed by disposing an undulating wire 22 having a top ribbon 60 of polymeric, non-textile graft material disposed over portions, such as medial portions, of the undulating wire 22, and a bottom ribbon 62 of polymeric, non-textile graft material disposed under portion, such as medical portions, of the undulating wire 22 onto a mandrel 58 as shown in FIG. 24. The ribbons 58, 60 may then be securably disposed to each other through lamination, sintering, adhesive bonding, and the like as described elsewhere herein. FIG. 25 depicts the ribbon stent-graft 10' after removal from the mandrel 58.

Figure 26:
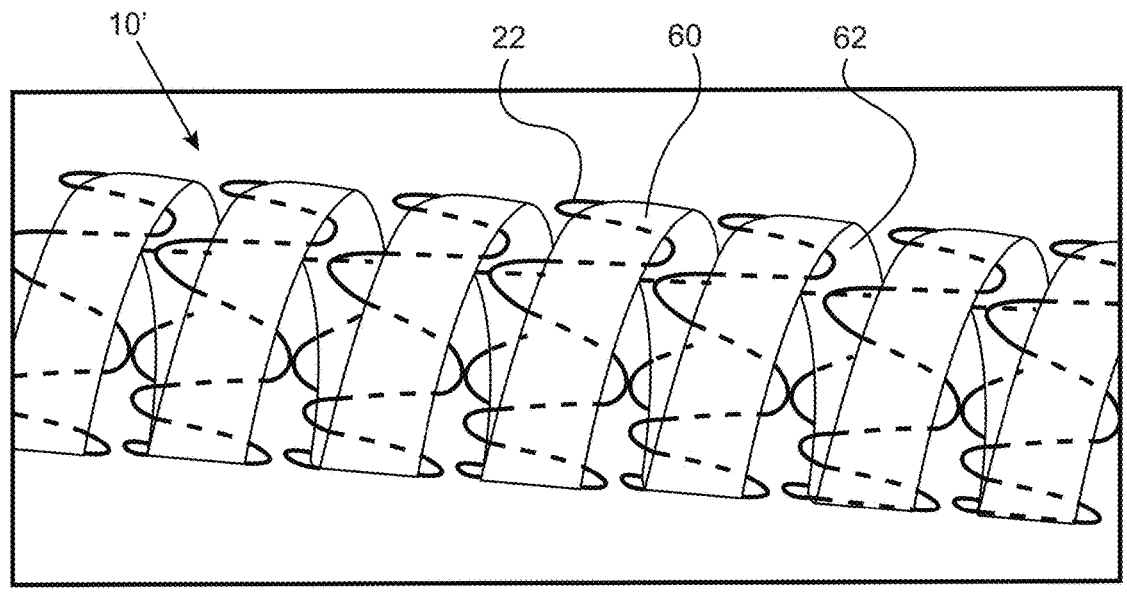

FIG. 26 is an enlarged view of a portion of the ribbon stent-graft 10' of FIG. 25 further detailing the device. As the ribbons 60, 62 are disposed only over medial portions of the undulating wire 22, the ribbons 60, 62 do not form a continuous graft wall. As a result, the ribbons 60, 62 freely move with movement of the undulating wire 22 of the ribbon stent-graft'. In other words the ribbons 60, 62 do not unduly inhibit movement of the undulating wire 22 upon longitudinal movement and/or bending.

Figure 27:
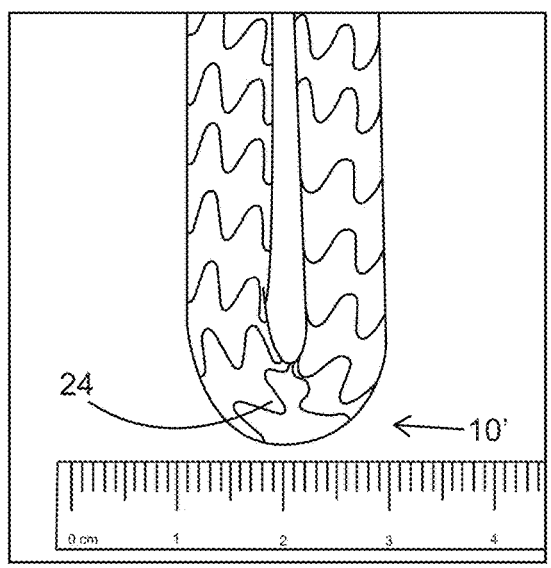
FIGS. 27 and 28 depict bending of an endovascular stent-graft according to the present inventive technology having the ribbon stent-graft of FIGS. 25 and 26.
Figure 28:
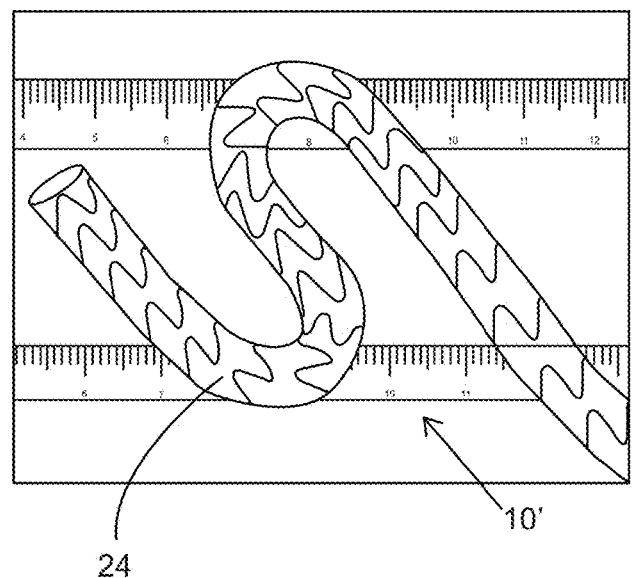

FIGS. 27 and 28 depict the flexibility of the stent-graft 10' while undergoing bending, including bending about 180° with about a 6 mm gap as described above and as depicted in FIG. 27. In FIGS. 27 and 28 the stent-graft 10' is disposed between a graft cover 24 and as graft liner as depicted in FIGS. 13A-15. FIG. 28 the depicts stent-graft 10' being subjected to multiple bending forces resulting in an "S" shaped stent-graft 10' with two major bends as may be experienced when deployed in certain anatomies, demonstrating increased flexibility and patency of the lumen of stent-graft 10' in a challenging configuration.

Figure 29:
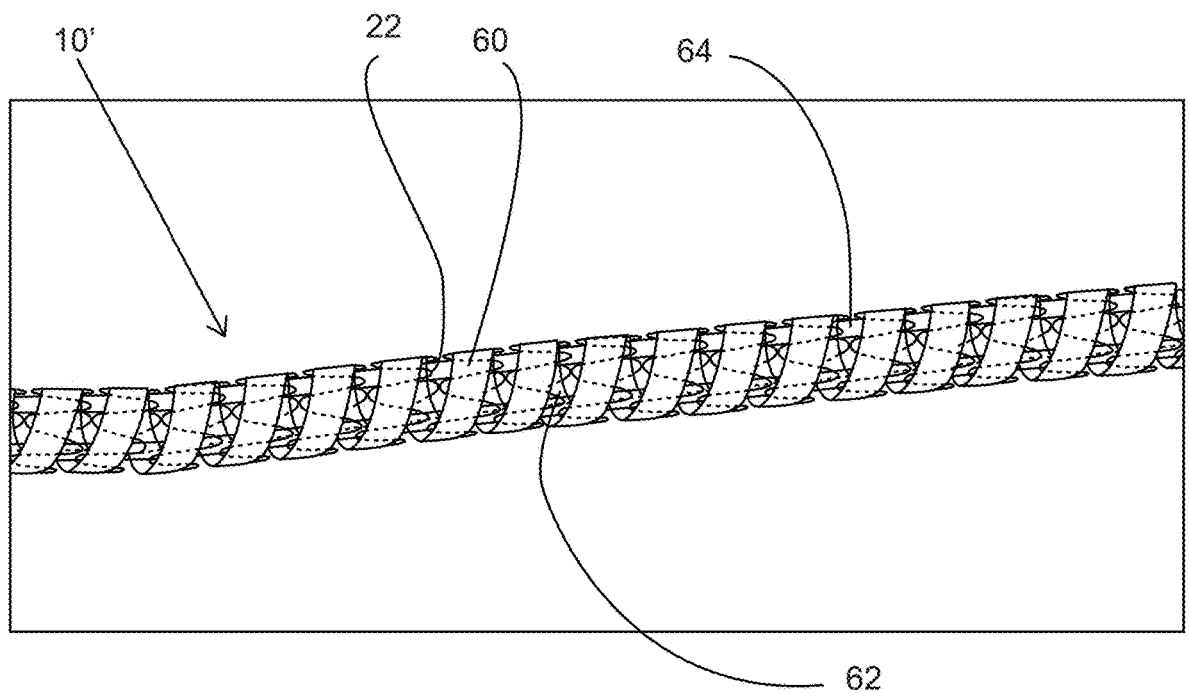
FIGS. 29 and 30 depict the ribbon stent-graft having an axial ribbon according to the present inventive technology.
Figure 30:
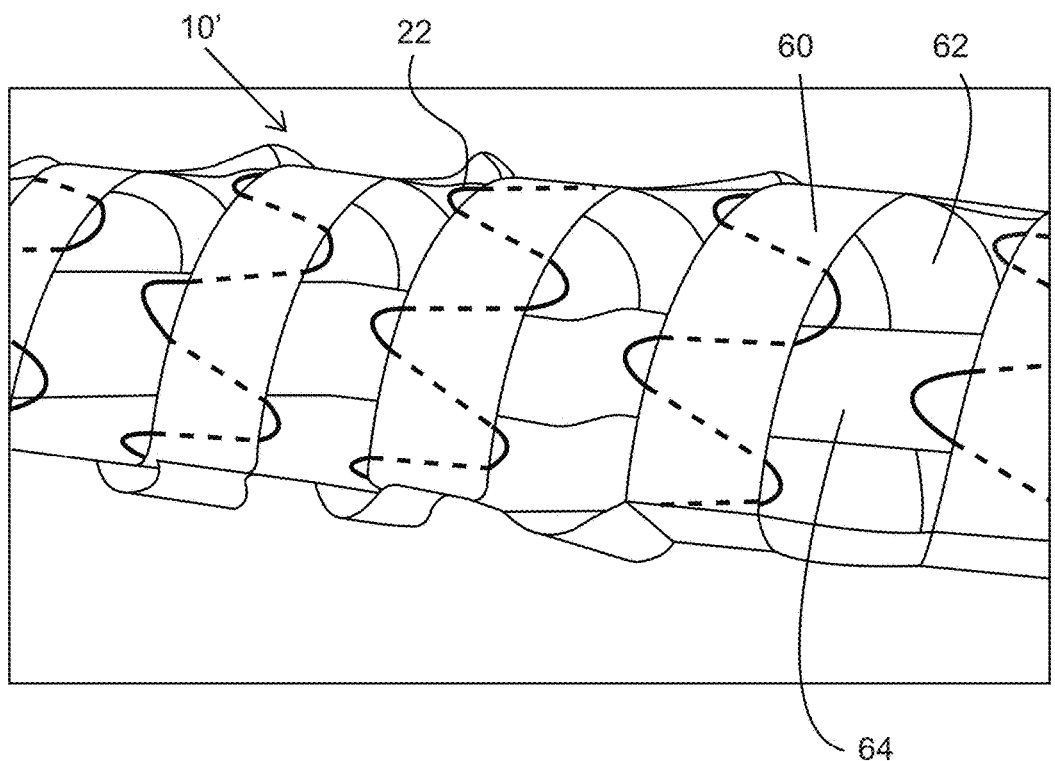
Figure 31:
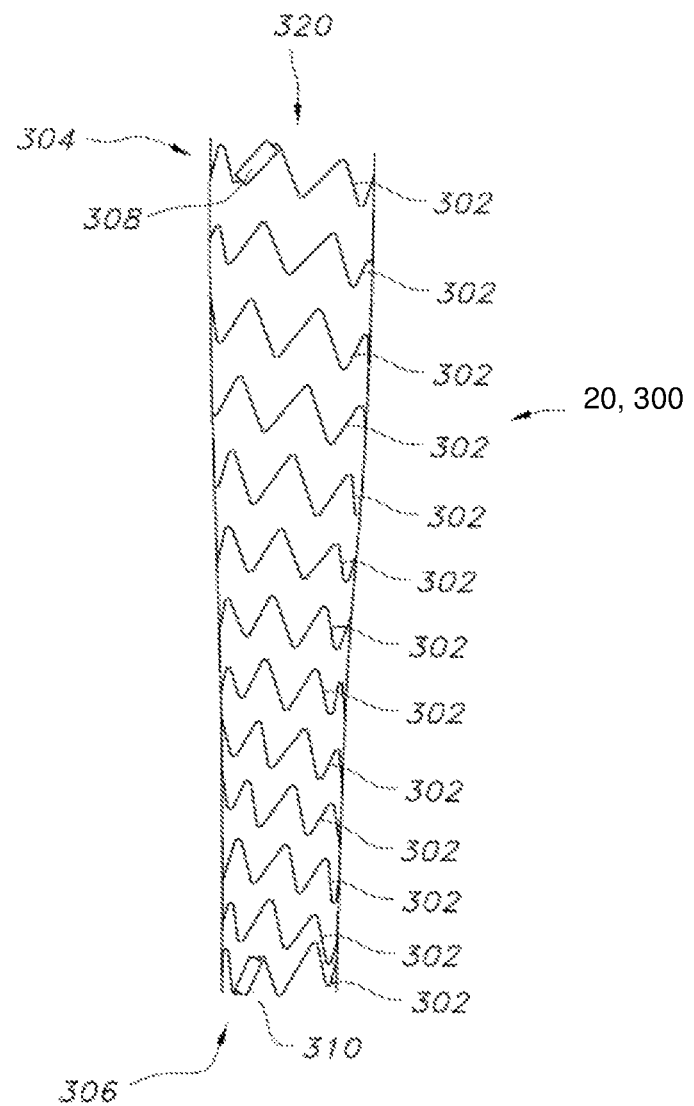
FIG. 31 depicts one embodiment of a stent structure useful in the present inventive technology.

As depicted in FIGS. 29 and 30 the ribbon stent-graft 10' may further include, if desired, an axial ribbon 64 disposed along the longitudinal length of the stent-graft 10'. Such an axial ribbon 64 will only slightly affect flexibility while providing for some increased control of the undulating wire 22 during longitudinal movement and/or bending and a design of the present technology that affords a different degree of stability and deployability in vivo.

Graft portions, such as covers and liners 24, 26, of the stent-grafts 10, 10' of the present inventive technology may include wall portions made from any biocompatible, durable material, including, for example polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. As used herein, textile materials are filaments or yarns that are woven, braided, knitted, filament-spun, and the like to form textile graft material. Desirably, the graft materials of the present inventive technology are non-textile graft materials, e.g., materials that are not woven, braided, knitted, filament-spun, etc. that may be used with textile grafts. Such useful graft material may be extruded materials. Particularly useful materials include porous polytetrafluoroethylene without discernible node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. PTFE layers lacking distinct, parallel fibrils that interconnect adjacent nodes of ePTFE and having no discernible node and fibril microstructure when viewed at a scanning electron microscope (SEM) magnification of 20,000 are also useful. A porous PTFE layer having no or substantially no fluid permeability may have a Gurley Number of greater than about 12 hours (43,200 seconds), or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Seconds is determined by measuring the time necessary for a given volume of air, typically, 25 cc, 100 cc or 300 cc, to flow through a standard 1 square inch of material or film under a standard pressure, such as 12.4 cm column of water. In contrast, embodiments of layers of PTFE discussed herein having low fluid permeability may have a Gurley Number of greater than about 1500 seconds where 100 cc of air is used in the test. Embodiments of fluid-permeable layers of PTFE, such as ePTFE, may have a Gurley measurement of less than about 10 or 15 Gurley seconds. Such testing maybe carried out with a Gurley Densometer, made by Gurley Precision Instruments, Troy, N.Y. Details of such useful PTFE materials and methods for manufacture of the same may be found in commonly owned U.S. Pat. No. 8,728,372 to Humphrey et al, entitled "PTFE Layers and Methods of Manufacturing", which is incorporated by reference in its entirety herein.

Furthermore, useful PTFE molecules have an average molecular weight of from about 20 million to about 50 million or more. Optionally, an additive, such as powdered or liquid color pigment or other resin additive may be added to the PTFE materials. For example, a fluorinated copolymer may be added (such as perfluoropropylvinylether-modified PTFE) to improve the bondability of PTFE layers. Additive is typically provided in a mass amount that is less than 2% of the mass of the PTFE material, but it may be provided in any amount that produces a desired result.

While porous PTFE layers may be configured to have low or substantially no fluid permeability, the porous PTFE layers 110 nonetheless have porosity. A porous PTFE layer may have an average porosity from about 20% to about 80%, and specifically from about 30% and about 70%. Porosity indicates the volume of solid PTFE material as a percentage of the total volume of the PTFE layer. An average pore size in the PTFE layer may be less than about 20 microns, and specifically less than about 0.5 micron, for example, from about 0.01 micron to about 0.5 micron. If tissue ingrowth is desired, the PTFE layer may have an average pore size of greater than about 6.0 microns.

The graft portions may be formed from an inner layer or layers and outer layer or layers of flexible graft material, such as PTFE or ePTFE. In one embodiment, the flexible graft material includes PTFE which is substantially porous but includes no discernable node and fibril structure. The inner and outer layers of graft material may be formed from tubular extrusions, laminated wraps of multiple layers of graft material or materials, and the like. The inner or outer layers of graft material may be permeable (e.g., less than about 10 Gurley seconds), semi-permeable (e.g., greater than about 1,500 Gurley seconds and optionally less than about 30,000) or substantially non-permeable (e.g., greater than about $10^6$ Gurley seconds) for some embodiments.

FIGS. 31-34B depict further details of the stent-grafts of the present inventive technology. A first radially expandable stent 20, 300 may be interposed between an outer layer (not shown) and inner layer (not shown) of graft material for these legs. The interposed stent disposed between the outer layer and inner layer of graft material may be formed from an elongate resilient element helically wound with a plurality of longitudinally spaced turns into an open tubular configuration. The helically wound stent may be configured to be a self-expanding stent or radially expandable in an inelastic manner actuated by an outward radial force from a device such as an expandable balloon or the like.

The stent or wire portions of the stent-grafts may be made from stainless steel, nickel titanium alloy (NiTi), such as NITINOL, or any other suitable material, including, but not limited to, cobalt-based alloy such as ELGILOY, platinum, gold, titanium, tantalum, niobium and combinations thereof. The stent-grafts may be balloon-expandable or self-expandable.

As shown in more detail in FIGS. 31, 32A-32B, 33A-33E and 34A-B, a generally tubular stent 20, 300 may be provided for the stent-grafts. The tubular stent 300 includes a helically-wound, undulating wire forming a series of adjacent helical windings 302, which may be made from the materials described above (including a resilient metal such as nitinol). The ends 304, 306 of the stent 300 may be secured to adjacent ring portions of the stent at distinct areas. For example, a first end may be adjoined via a first securement point 308, and a second end may be joined at a second securement point 310, as shown to avoid exposure of element ends to either PTFE graft material or possible patient tissues. In a preferred embodiment, the securement points 308, 310 are located proximal to the first end 304 and second end 306, respectively, with no other securement points on the stent 300. That is, aside from the helical windings 302 at the first end 304 (which may be referred to as a proximal end 304) and second end 306 (which may be referred to as a distal end 306), respectively, adjacent approximate circumferential windings 302 in the stent 300 may be free of interconnecting securement points. Any securement means may be used, including, for example, welding, such as struts and welds. It is desired that the relative stiffness of a stent be greater than the stiffness of the PTFE graft material so as to provide beneficial kink resistance.

The undulating wire may be a continuous element forming a series of helical windings 302 extending from one end 304 of the extension to the other end 306 thereof. The tubular stent 300 thus has an internal lumen 320 extending there through, from the first end 304 to the second end 306. The ends 304, 306 of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch. As may be seen in FIGS. 32A and 32B, the stent 300 may be tapered or flared. In addition, if desired, adjacent helical windings 302 may be arranged 315 such that adjacent helical windings 302 at one end (either the first end 304 or second end 306) have an acute angle formation at a portion of the stent 300 proximal to the end of the stent 300. That is, if desired, the helical winding closest to the end (shown as 302') may have an approximately 180° angle with respect to the longitudinal axis, while the helical winding next to this helical winding (shown as 302") has an angle less than 180°. These two helical windings (302' and 302") may be attached at securement points 308, 310.

FIGS. 33A through 33E depicts various arrangements of the helical windings 302 formed by the undulating wire in forming the stent 300. Adjacent helical windings are depicted as 302A and 302B, but it will be understood that the arrangement depicted in FIGS. 33A through 33E may be applied to each helical winding 302 in the stent 300. Alternatively, the arrangements depicted in FIGS. 33A through 33E may be applied to only some of the helical windings 302 in the stent 300. Undulating wire of the stent 300 includes a series of peaks 312 and valleys 314 as the wire is helically wound. The arrangement of peaks 312 and valleys 314 may vary and may be arranged in any fashion desired. In some embodiments, such as that of FIG. 33A, the peaks 312 of one circumferential winding 302A may be substantially aligned with the peaks 312 of an adjacent circumferential winding 302B. As can be seen in FIG. 33B, the adjacent circumferential windings 302A and 302B may be spaced apart. As can be seen in FIG. 33C, the adjacent circumferential windings 302A and 302B may be closer together. In another embodiment, set forth in FIG. 33D, one peak 312 of one circumferential winding 302B may span two peaks 312 of an adjacent winding 302A. In another embodiment set forth in FIG. 33E, the peaks 312 of one circumferential winding 302A may be substantially aligned with the valleys 314 of an adjacent circumferential winding 302B. Other arrangements for the helical windings 302 are contemplated and will be readily understood by those of skill in the art.

The distances between adjacent windings 302A, 302B may vary along the length of the stent 300, where the distance at one end 304 is different than the distance at the second end 306. In each embodiment, there are two distances that should be considered. The first distance X is the distance between the lowest valley (314) of the first winding (302A) and the highest peak (312) of the second winding (302B). The second distance Y is the distance between the highest peak (312) and lowest valley (314) of the first winding (302A).

There may be at least two different ratios of X/Y (or equivalently X/Y) present in the device, including but limited to three different relative ratios of these distances X/Y. The first ratio is where X/Y is a relatively large positive number, that is, there is a relatively larger separation between the distance (X) as compared to the distance (Y). The second ratio is where X/Y is a relatively smaller positive number, that is, there is a relatively smaller separation between the distance (X) as compared to the distance (Y). Finally, the third ratio is where X/Y is a negative number, that is, the lowest peak of the first winding (302A) dips to a point lower than the highest peak of the second winding (302B).

The ratio X/Y can be manipulated to obtain the desired properties of the stent-graft in a local region. A relatively large X/Y ratio (preferably greater than about 0.5) produces a highly flexible region of a stent-graft. A smaller X/Y ratio (preferably from about 0.1 to about 0.5) produces regions of a stent-graft with moderate flexibility and moderate radial force. A region of a stent-graft with an even smaller or negative X/Y ratio (preferably less than about 0.1) has a relatively high radial force with relatively less flexibility. The above ranges for X/Y are appropriate when the stent height Y is from about one-third of the diameter of the stent to about equal to the diameter of the stent. If Y is larger than this when compared to D, then the ranges for the X/Y ratios quoted above will be reduced. Similarly, if Y is much smaller than the stent diameter D, then the numerical values for the ranges above will be increased.

Using the principle described above, a stent-graft can be constructed with varying ratios of X/Y along the length to achieve desired properties. For example, if a stent-graft is used as an iliac limb in a modular endovascular graft for abdominal aortic aneurysms (AAAs), it may be desirable for the proximal end of the stent-graft to have a relatively high radial force to maximize anchorage into the aortic body component of the modular system. In this case, the proximal end of the iliac limb could be designed with a small or negative X/Y ratio, such as −0.5, and Y may be chosen to be, for example, from about one fifth to one half of the stent-graft diameter. In this region flexibility is less important than radial force so the negative X/Y ratio yields the desired properties. In the middle of the stent-graft flexibility becomes important to accommodate the tortuous common iliac arteries often found in AAA patients. It may then be desirable to have a relatively large X/Y ratio, such as about 0.55, to achieve this flexibility. Near the distal end of the stent-graft it may again be desirable to have more radial force to promote anchorage and sealing of the iliac limb into the common iliac artery of the patient, but not as much radial force as at the proximal end. In this case, it may be desirable to have an X/Y ratio near zero, or from about −0.1 to about 0.3.

Since the stent is formed in a helix along the length of the stent-graft, it is possible to continuously vary the X/Y ratio to achieve the desired properties in various regions of the stent-graft with smooth variations and no abrupt changes along the length. These smooth variations promote conformance to the vasculature and avoid the stress and/or strain concentrations and potential kinking that can result from abrupt transitions in mechanical properties along the length of a stent-graft.

Figures 32A, 32B:
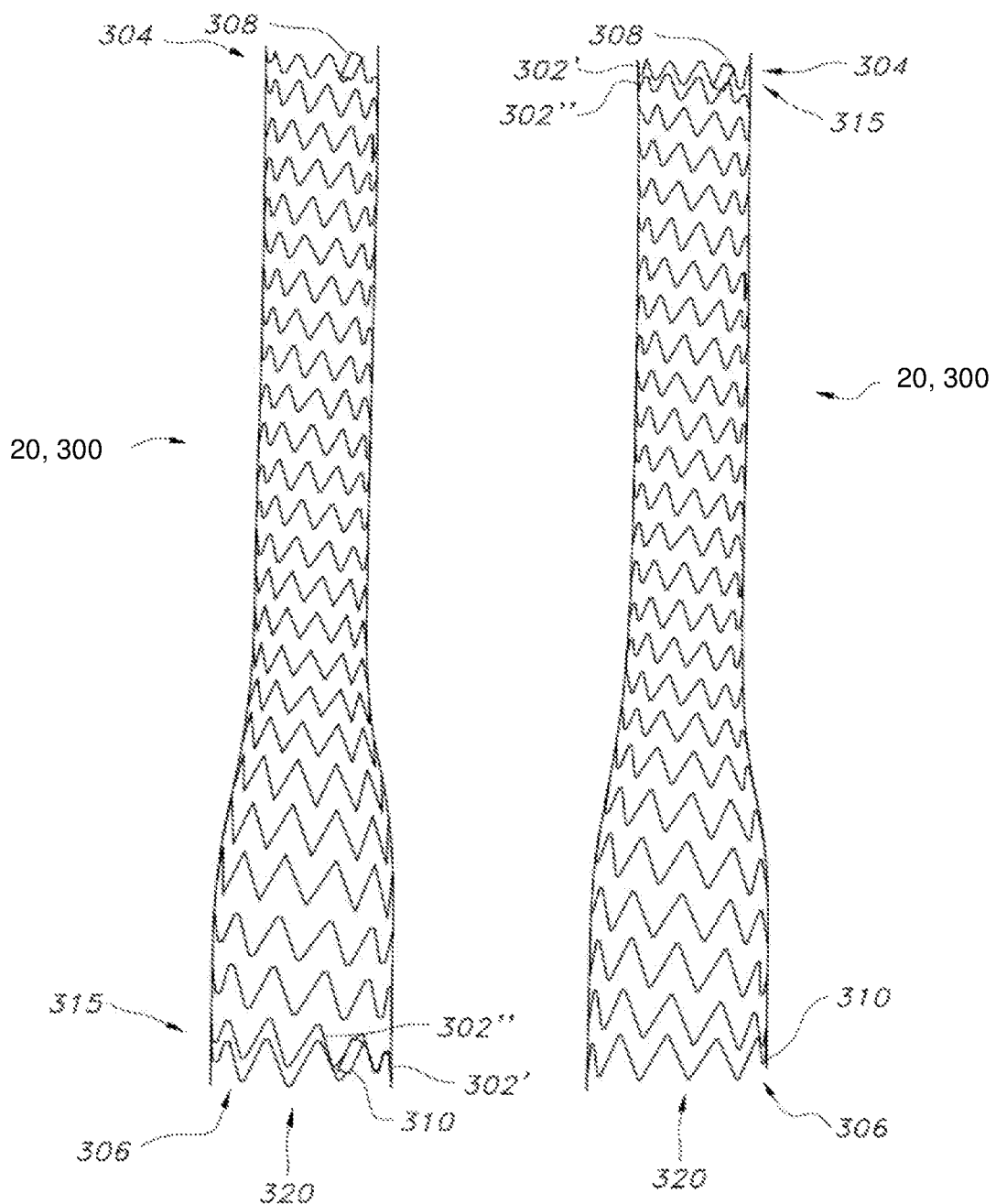
FIGS. 32A and 32B depict various embodiments of stent structures useful in the present inventive technology.

The stent 300 may include a longitudinal axis (generally defined along internal lumen 320) and a radial axis perpendicular to the longitudinal axis; where the helical windings 302 are wound at an acute winding angle of about 3 degrees to about 15 degrees with respect to the radial axis. As can be seen in FIGS. 32A and 32B, the acute winding angle at a portion of the stent 300 proximal to the first end 304 is different from the acute winding angle at a portion of the stent 300 proximal to the second end 306. In some embodiments, a first helical winding 302 at the first end 304 may be perpendicular to the longitudinal axis. Further, it may be desired that a helical winding 302 at the second end 306 is perpendicular to the longitudinal axis. Helical windings 302 at the first end 304 and the second end 306 may both be perpendicular to the longitudinal axis, or only one may be perpendicular to the longitudinal axis. An adjacent peak 312 and an adjacent valley 314 of a helical winding 302 have a peak height from an apex of said adjacent peak to a base of said adjacent valley. It may be desired that the peak height at a portion of the stent 300 proximal to the first end 304 of the stent 300 is different from the peak height at a portion of the stent 300 proximal to the second end 306 of the stent 300.

At least one graft layer may be disposed on the stent 300 with the embodiments described herein. The placement of the graft layers may best be seen in FIGS. 34A, 34B and 30. In some embodiments, an inner graft layer 318 may be disposed on the interior surface of the helically wound stent 300, forming inner lumen 320. A second graft layer 316 may be disposed on the outer surface of the helically wound stent 300 with the embodiments described herein, forming an outside surface. More than one or two layers of graft material may be disposed on the interior or exterior of the helically wound stent 300 as desired. For some embodiments of stent-grafts, layers of materials having different properties may be used in combination to achieve a desired clinical performance. For example, some layers of PTFE covering the stent 300 may be permeable, semi-permeable or substantially non-permeable depending on the desired performance and material properties. The layers 316 and 318 may be applied by a variety of methods and have a variety of configurations as described herein. For example, some layer embodiments may include extruded tubular structures applied axially over a mandrel or subassembly. Some layer embodiments 316 and 318 may be applied by wrapping layers circumferentially or wrapping tapes or ribbons in an overlapping helical pattern. For some embodiments, the outer layer 316 may be made from or include a semi-permeable or substantially non-permeable PTFE layer and the inner layer 318 may be made of or include a permeable layer of PTFE.

The stent-grafts may be made by forming the layers of material 316, 318 together with the helically wound stent 300 over a mandrel, such as a cylindrical mandrel (not shown). Once the innermost layer 316 of the stent-graft has been wrapped about a shaped mandrel, a helical nitinol stent, such as helical stent 300, may be placed over the innermost layered PTFE layer 316 and underlying mandrel. If desired, one or more additional layers 318 of graft material may be wrapped or otherwise added over the exterior of the stent 300 as described herein. If desired, the outer layer 318 may include low permeability PTFE film or PTFE film having substantially no permeability that does not have the traditional node fibril microstructure.

The graft portions may be made at least partially from polytetrafluoroethylene (PTFE) which may include expanded polytetrafluoroethylene (ePTFE). In particular, graft portions may include any number of layers of PTFE and/or ePTFE, including from about 2 to about 15 layers, having an uncompressed layered thickness of about 0.003 inches to about 0.015 inches for the supple graft material or materials alone without supporting or ancillary structures such as high strength stents, connector rings or the like. Such graft body sections may also include any alternative high strength, supple biocompatible materials, such as DACRON, suitable for graft applications. Descriptions of various constructions of graft body sections as well as other components of graft assembly that may be used in any suitable combination for any of the embodiments discussed herein may be found in U.S. Pat. No. 7,125,464 to Chobotov et al., entitled "Method and Apparatus for Manufacturing an Endovascular Graft Section"; U.S. Pat. No. 7,090,693 to Chobotov et al., entitled "Endovascular Graft Joint and Method of Manufacture"; U.S. Pat. No. 7,147,661, entitled "Method and Apparatus for Shape Forming Endovascular Graft Material", to Chobotov et al.; U.S. Pat. No. 7,147,660 to by Chobotov et al., entitled "Advanced Endovascular Graft"; and U.S. Pat. No. 8,728,372 to Humphrey et al., entitled "PTFE Layers and Methods of Manufacturing"; the entirety of each of which is incorporated herein by reference.

Additional details of the above-described graft assemblies, including modular components, may be found in U.S. Patent Application Publication No. 2013/0261734 to Young et al., entitled "Advanced Kink Resistant Stent-graft"; the entirety of which is incorporated herein by reference. Moreover, additional details of graft and stent-graft assemblies, including modular components, may be found in U.S. Patent Application Publication No. 2015/0088244 to Chobotov, entitled "Tandem Modular Endograft"; the entirety of which is incorporated herein by reference.

Various methods of delivery systems and delivery of the device into a patient include those described in U.S. Patent Application Publication No. 2009/0099649 to Chobotov et al., entitled "Modular Vascular Graft for Low Profile Percutaneous Delivery", the contents of which are incorporated by reference in entirety herein. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and a delivery catheter may be directly inserted into the patient's access vessel by either arteriotomy or percutaneous puncture.

The systems, devices, methods and techniques of the present inventive technology may be used together with systems, devices, methods and techniques for treating abdominal aortic aneurysms. Details of the endovascular prosthesis and/or graft extensions useful for treating abdominal aortic aneurysms may be found in commonly owned U.S. Pat. Nos. 6,395,019; 7,081,129; 7,147,660; 7,147,661; 7,150,758; 7,615,071; 7,766,954 and 8,167,927 and commonly owned U.S. Published Application No. 2009/0099649, the contents of all of which are incorporated herein by reference in their entirety. Details for the manufacture of such endovascular prostheses may be found in commonly owned U.S. Pat. Nos. 6,776,604; 7,090,693; 7,125,464; 7,147,455; 7,678,217 and 7,682,475, the contents of all of which are incorporated herein by reference in their entirety. Useful inflation materials for the inflatable grafts may be found in may be found in commonly owned U.S. Published Application No. 2005/0158272 and 2006/0222596, the contents of all of which are incorporated herein by reference in their entirety. Additional details of suitable endovascular delivery systems for abdominal aortic aneurysms include, but are not limited to U.S. Pat. Nos. 9,233,015, 9,066,828 and 9,132,025, the contents of which are incorporated herein by reference in their entirety.

While various embodiments of the present inventive technology are specifically illustrated and/or described herein, it will be appreciated that modifications and variations of the present inventive technology may be effected by those skilled in the art without departing from the spirit and intended scope of the inventive technology. Further, any of the embodiments or aspects of the invention as described in the claims or in the specification may be used with one and another without limitation.

The following embodiments or aspects of the invention or inventive technology may be combined in any fashion and combination and be within the scope of the present invention, as follows:

Embodiment 1. An endovascular stent-graft (10) comprising:
 a tubular stent wall (12) having opposed first and second ends (14, 16);
 an undulating wire (22) having a thickness (37) and having opposed first and second ends and being helically wound into a plurality of approximate circumferential windings to define the stent wall (12);
 the undulating wire (22) having a plurality of undulations defined by peaks (28) and valleys (30) with peaks of adjacent approximate circumferential windings being separated by a distance;
 the first wire end secured to a first undulation at the first end;
 the second wire end secured to a second undulation at the second end;
 a graft liner (26) comprising a layer of non-textile, polymeric graft material; and
 a graft cover (24) comprising a layer of non-textile, polymeric graft material;
 wherein the graft liner (26) and the graft cover (24) are selectively secured to each other defining secured graft portions (36) thereat and defining non-secured graft portions (38) therein between, the non-secured graft portions (38) defining a graft cavity (38) between the graft liner (26) and the graft cover (24);
 wherein the tubular stent wall is disposed within the graft cavity (38); and
 wherein the graft cavity (38) has a longitudinal extent (39) greater than the thickness (39) of the undulating wire (22).

Embodiment 2. The endovascular stent-graft (10) of embodiment 1, wherein the secured graft portions (36) have a longitudinal extent (35) of about the thickness (37) of the undulating wire (22) or greater.

Embodiment 3. The endovascular stent-graft (10) of embodiment 1, wherein the secured graft portions (36) have a longitudinal extent (35) of about the thickness (37) of the undulating wire (22) or less.

Embodiment 4. The endovascular stent-graft (10) of embodiment 1, wherein, except for the first and the second wire ends being secured to the first and second undulations, respectively, adjacent approximate circumferential windings are free of interconnecting struts and welds.

Embodiment 5. The endovascular stent-graft (10) of embodiment 1, wherein the layer of non-textile, polymeric graft material for the graft cover (24) comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

6. The endovascular stent-graft (10) of embodiment 1, wherein the layer of non-textile, polymeric graft material for the graft liner (26) comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 7. The endovascular stent-graft (10) of embodiment 1, wherein the graft liner (26) and the graft cover (24) laminated or adhesively bonded each other at the secured graft portions (36).

Embodiment 8. The endovascular stent-graft (10) of embodiment 1, wherein the undulating wire (22) is not secured to the graft liner (26) and graft cover (24) within the graft pocket (38).

Embodiment 9. An endovascular stent-graft (10) comprising:
 a tubular stent wall (12) having opposed first and second ends (14,16);
 an undulating wire (22) having a thickness (37) and having opposed first and second ends and being helically wound into a plurality of approximate circumferential windings to define the stent wall (12);
 the undulating wire (22) having a plurality undulations defined by peaks and valleys with peaks of adjacent approximate circumferential windings being separated by a distance;

the first wire end secured to a first undulation at the first end;

the second wire end secured to a second undulation at the second end;

a graft liner (26) having opposed first and second end portions and a medial portion therein between, the graft liner (26) comprising a layer of non-textile, polymeric graft material; and a graft cover (24) having opposed first and second end portions and a medial portion therein between, the graft liner (24) comprising a layer of non-textile, polymeric graft material;

wherein the first end portion of the graft liner (26) and the first end portion of the graft cover (24) are secured to each other to define a fused first end (48);

wherein the second end portion of the graft liner (26) and the second end portion of the graft cover (24) are secured to each other to define a fused second end (50);

wherein at least one portion of the medial portions of the graft cover (24) and the graft liner (26) are not secured to each other defining a non-secured graft portion (38) thereat, the non-secured graft portion (38) defining a graft cavity (38) between the graft liner (26) and the graft cover (24); and wherein the tubular stent wall (12) is disposed within the graft cavity (38).

Embodiment 10. The endovascular stent-graft (10) of embodiment 9, further comprising a plurality of non-secured graft portions (38).

Embodiment 11. The endovascular stent-graft (10) of embodiment 9, wherein the non-secured graft portion (38) extends substantially along the medial portions of the graft cover (24) and graft liner (26).

Embodiment 12. The endovascular stent-graft (10) of embodiment 9, wherein the graft cover (24) between the first and second ends (48, 50) comprises a pleated portion (44, 46).

Embodiment 13. The endovascular stent-graft (10) of embodiment 9, wherein the graft cover (24) between the first and second ends (48, 50) comprises a crimped portion (44).

Embodiment 14. The endovascular stent-graft (10) of embodiment 9, wherein, except for the first and the second wire ends being secured to the first and second undulations, respectively, adjacent approximate circumferential windings are free of interconnecting struts and welds.

Embodiment 15. The endovascular stent-graft (10) of embodiment 9, wherein the layer of non-textile, polymeric graft material for the graft cover comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 16. The endovascular stent-graft (10) of embodiment 9, wherein the layer of non-textile, polymeric graft material for the graft liner comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 17. The endovascular stent-graft (10) of embodiment 9, wherein the graft liner (26) and the graft cover (24) are laminated or adhesively bonded each other at the secured graft portions (36).

Embodiment 18. An endovascular stent-graft (10) comprising a ribbon stent-graft (10'); the ribbon stent-graft (10') comprising:

a tubular stent wall having opposed first and second ends;

an undulating wire (22) having a thickness (37) and having opposed first and second ends and being helically wound into a plurality of approximate circumferential windings to define the stent wall;

the undulating wire (22) having a plurality undulations defined by (28) peaks and (30) valleys with medial wire portions (32) coextensive with the peaks (28) and (30) valleys, wherein the peaks of adjacent approximate circumferential windings are separated by a distance;

the first wire end secured to a first undulation at the first end;

the second wire end secured to a second undulation at the second end;

an elongate planar ribbon liner (62) having opposed first and second end portions and a medial portion therein between, the planar ribbon liner (62) comprising a layer of non-textile, polymeric graft material; and an elongate planar ribbon cover (60) having opposed first and second end portions and a medial portion therein between, the planar ribbon liner comprising a layer of non-textile, polymeric graft material;

wherein the elongate ribbon cover (60) is disposed over the medial wire portions (32);

wherein the elongate ribbon liner (62) is disposed under the medial wire portions (32); and wherein the elongate ribbon cover (60) and the elongate ribbon liner (62) are securably disposed to each other and to the medial wire portions (32).

Embodiment 19. The endovascular stent-graft (10) of embodiment 18, a width of the elongate ribbon cover (60) and a width of the elongate ribbon liner (62) do not extend to the peaks (28) and valleys (30) of the undulating wire (22).

Embodiment 20. The endovascular stent-graft (10) of embodiment 18, further comprising:

a tubular graft liner (26) having opposed first and second end portions and a medial portion therein between, the graft liner (26) comprising a layer of non-textile, polymeric graft material; and a tubular graft cover (24) having opposed first and second end portions and a medial portion therein between, the graft cover (24) comprising a layer of non-textile, polymeric graft material;

wherein the first end portion of the tubular graft liner (26) and the first end portion of the tubular graft cover (24) are secured to each other to define a fused first end (48);

wherein the second end portion of the tubular graft liner (26) and the second end portion of the tubular graft cover (24) are secured to each other to define a fused second end (50);

wherein at least one portion of the medial portions of the tubular graft cover (24) and the tubular graft liner (26) are not secured to each other defining a non-secured tubular graft portion (38) thereat, the non-secured tubular graft portion (38) defining a graft cavity (38) between the tubular graft liner (26) and the tubular graft cover (24); and wherein the ribbon stent-graft (10') is disposed within the graft cavity (38).

Embodiment 21. The endovascular stent-graft (10) of embodiment 20, further comprising a plurality of non-secured tubular graft portions (36).

Embodiment 22. The endovascular stent-graft (10) of embodiment 20, wherein the non-secured tubular graft portion (38) extends substantially along the medial portions of the graft cover (24) and graft liner (26).

Embodiment 23. The endovascular stent-graft (10) of embodiment 20, wherein the tubular graft cover (24) between the first and second ends (48, 50) is configured to form a pleated portion (44, 46) upon longitudinal compression or axial bending of the endovascular stent-graft (10).

Embodiment 24. The endovascular stent-graft (10) of embodiment 20, wherein the tubular graft cover (24) between the first and second ends (48, 50) is configured to form a crimped portion (44) upon longitudinal compression or axial bending of the endovascular stent-graft (10).

Embodiment 25. The endovascular stent-graft (10) of embodiment 19, wherein, except for the first and the second wire ends being secured to the first and second undulations, respectively, adjacent approximate circumferential windings are free of interconnecting struts and welds.

Embodiment 26. The endovascular stent-graft (10) of embodiment 19, wherein the layer of non-textile, polymeric graft material for the elongate ribbon cover (60) comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 27. The endovascular stent-graft (10) of embodiment 19, wherein the layer of non-textile, polymeric graft material for the elongate ribbon liner (62) comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 28. The endovascular stent-graft (10) of embodiment 20, wherein the layer of non-textile, polymeric graft material for the tubular graft cover (24) comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 29. The endovascular stent-graft (10) of embodiment 20, wherein the layer of non-textile, polymeric graft material for the tubular graft liner (26) comprises polytetrafluoroethylene selected from the group consisting of porous polytetrafluoroethylene having no discernible node and fibril microstructure, expanded polytetrafluoroethylene having a node and fibril microstructure, polytetrafluoroethylene having low or substantially no fluid permeability which includes a closed cell microstructure having high density regions having grain boundaries directly interconnected to grain boundaries of adjacent high density regions and having substantially no node and fibril microstructure, porous polytetrafluoroethylene having no or substantially no fluid permeability; semi-permeable polytetrafluoroethylene, permeable polytetrafluoroethylene, and combinations thereof.

Embodiment 30. The endovascular stent-graft (10) of embodiment 20, wherein the tubular graft liner (26) and the tubular graft cover (24) are laminated or adhesively bonded each other at the secured graft portions (36).

Embodiment 31. The endovascular stent-graft (10) of embodiment 1, wherein the endovascular stent-graft (10) is configured to bend about 180° with about a 6 mm gap or less between portions of the graft cover (24) proximal the bend; and wherein the endovascular stent-graft (10) maintains a substantially tubular shape through the bend.

Embodiment 32. The endovascular stent-graft (10) of embodiment 9, wherein the endovascular stent-graft (10) is configured to bend about 180° with about a 6 mm gap or less between portions of the graft cover (24) proximal the bend; and wherein the endovascular stent-graft (10) maintains a substantially tubular shape through the bend.

Embodiment 33. The endovascular stent-graft (10) of embodiment 20, wherein the endovascular stent-graft (10) is configured to bend about 180° with about a 6 mm gap or less between portions of the tubular graft cover (24) proximal the bend; and wherein the endovascular stent-graft (10) maintains a substantially tubular shape through the bend.

Embodiment 34. The endovascular stent-graft (10) of embodiment 1, wherein the endovascular stent-graft (10) is configured to bend about 180° or greater without the endovascular stent-graft (10) having a substantial reduction in diameter in a portion of the bend.

Embodiment 35. The endovascular stent-graft (10) of embodiment 9, wherein the endovascular stent-graft (10) is configured to bend about 180° or greater without the endovascular stent-graft (10) having a substantial reduction in diameter in a portion of the bend.

Embodiment 36. The endovascular stent-graft (10) of embodiment 20, wherein the endovascular stent-graft (10) is configured to bend about 180° or greater without the endovascular stent-graft (10) having a substantial reduction in diameter in a portion of the bend.

Embodiment 37. The endovascular stent-graft (10) of embodiment 1, wherein the secured graft portions (36) lack sutures.

Embodiment 38. The endovascular stent-graft (10) of embodiment 9, wherein secured graft portions (36) of the graft liner (26) and the graft cover (24) lack sutures.

Embodiment 39. The endovascular stent-graft (10) of embodiment 20, wherein secured tubular graft portions (36) of the tubular graft liner (26) and the tubular graft cover (24) lack sutures.

The invention claimed is:

1. An endovascular stent-graft comprising:
   an undulating wire helically wound into a plurality of approximate circumferential windings;
   the undulating wire having a plurality of undulations defined by peaks and valleys with peaks of adjacent approximate circumferential windings being separated by a distance;
   a graft liner; and
   a graft cover;
   wherein the graft liner and the graft cover are selectively secured to each other with a combination of heat and compression, defining secured graft portions thereat and defining non-secured graft portions therein between;
   wherein the graft liner and the graft cover are at least partially secured to each other in a first area entirely bounded by a first valley, a first peak, and a second valley of a particular approximate circumferential winding of the plurality of approximate circumferential windings of the undulating wire, and wherein the graft liner and the graft cover are entirely unsecured to each other in a second area which surrounds the first area and is bounded by the first valley, the first peak, and a second valley of the particular approximate circumferential winding of the undulating wire; and
   wherein the secured graft portions that are selectively secured to each other by applying a combination of heat and compression, the combination of heat and compression is applied along a contoured line following a contour defined by the first valley, the first peak, the second valley, a first medial portion positioned between the first valley and the first peak, and a second medial portion positioned between the second valley and the first peak.

2. The endovascular stent-graft of claim 1, wherein the secured graft portions have a longitudinal extent that is greater than a thickness of the undulating wire.

3. The endovascular stent-graft of claim 1, wherein the secured graft portions have a longitudinal extent that is less than a thickness of the undulating wire.

4. The endovascular stent-graft of claim 1, wherein adjacent approximate circumferential windings are free of interconnecting struts and welds.

5. The endovascular stent-graft of claim 1, wherein the undulating wire is helically wound into a plurality of approximate circumferential windings to define a tubular stent wall, and the tubular stent wall is disposed at least partially between the graft liner and the graft cover.

6. The endovascular stent-graft of claim 1, wherein the graft liner and the graft cover are laminated or adhesively bonded to each other at the secured graft portions.

7. The endovascular stent-graft of claim 1, wherein the first valley, the first peak, the second valley, and the second peak of the particular approximate circumferential winding of the undulating wire are not secured to the graft liner and graft cover.

8. The endovascular stent-graft of claim 1, wherein the endovascular stent-graft is configured to bend 180° with a 6 mm gap or less between portions of the graft cover proximal the bend; and wherein the endovascular stent-graft maintains a tubular shape through the bend.

9. The endovascular stent-graft of claim 1, wherein the endovascular stent-graft is configured to bend 180° or greater without the endovascular stent-graft having a reduction in diameter in a portion of the bend.

10. The endovascular stent-graft of claim 1, wherein the area securing the graft liner and the graft cover is linear having a first end and a second end and nested adjacent to the first peak.

11. The endovascular stent-graft of claim 1, wherein the area securing the graft liner and the graft cover is a bent linear segment having a first end, a second end and a peak therebetween.

12. An endovascular stent-graft comprising:
    an undulating wire helically wound into a plurality of approximate circumferential windings;
    the undulating wire having a plurality undulations defined by peaks and valleys with peaks of adjacent approximate circumferential windings being separated by a distance;
    a graft liner having opposed first and second end portions; and
    a graft cover having opposed first and second end portions;
    wherein the first end portion of the graft liner and the first end portion of the graft cover are secured to each other with a combination of heat and compression to define a fused first end;
    wherein the second end portion of the graft liner and the second end portion of the graft cover are secured to each other with a combination of heat and compression to define a fused second end;
    wherein the graft liner and the graft cover are at least partially secured to each other in a first area entirely bounded by a first valley, a first peak, and a second valley of a particular approximate circumferential winding of the plurality of approximate circumferential windings of the undulating wire, and wherein the graft liner and the graft cover are entirely unsecured to each other in a second area which surrounds the first area and is bounded by the first valley, the first peak, and the second valley of the particular approximate circumferential winding of the undulating wire; and
    wherein the portions of the graft liner and the graft cover that are secured to each other by applying a combination of heat and compression, the combination of heat and compression is applied along a contoured line following a contour defined by the first valley, the first peak, the second valley, a first medial portion positioned between the first valley and the first peak, and a second medial portion positioned between second valley and the first peak.

13. The endovascular stent-graft of claim 12, further comprising a plurality of non-secured graft portions at which the graft cover and the graft liner are not secured to each other, wherein at least one non-secured graft portion of the non-secured graft portions extends along the medial portions of the graft cover and graft liner.

14. The endovascular stent-graft of claim 12, wherein the graft cover between the first and second ends comprises a pleated portion.

15. The endovascular stent-graft of claim 12, wherein the graft cover between the first and second ends comprises a crimped portion.

16. The endovascular stent-graft of claim 12, wherein adjacent approximate circumferential windings are free of interconnecting struts and welds.

17. The endovascular stent-graft of claim 12, wherein the graft liner and the graft cover are laminated or adhesively bonded to each other within the area bounded by the first valley, the first peak, and the second valley of the particular approximate circumferential winding of the undulating wire.

18. The endovascular stent-graft of claim 12, wherein the endovascular stent-graft is configured to bend 180° with a 6 mm gap or less between portions of the graft cover proximal the bend; and wherein the endovascular stent-graft maintains a tubular shape through the bend.

19. The endovascular stent-graft of claim 12, wherein the endovascular stent-graft is configured to bend 180° or greater without the endovascular stent-graft having a reduction in diameter in a portion of the bend.

20. An endovascular stent-graft comprising:
- an undulating wire helically wound into a plurality of approximate circumferential windings, the undulating wire having a plurality of undulations defined by peaks and valleys;
- a graft liner; and
- a graft cover;

wherein the graft liner and the graft cover are selectively secured to each other with a combination of heat and compression, defining secured graft portions thereat and defining non-secured graft portions therein between, wherein the graft liner and the graft cover are at least partially secured to each other in a first area, and wherein the graft liner and the graft cover are entirely unsecured to each other in a second area which completely surrounds the first area; and wherein the secured graft portions that are selectively secured to each other by applying a combination of heat and compression, the combination of heat and compression is applied along a contoured line following a contour defined by a first valley of an approximate circumferential winding of the plurality of approximate circumferential windings of the undulating wire, a first peak of the approximate circumferential winding of the plurality of approximate circumferential windings of the undulating wire, a second valley of the approximate circumferential winding of the plurality of approximate circumferential windings of the undulating wire, a first medial portion positioned between the first valley and the first peak, and a second medial portion positioned between the second valley and the first peak.

* * * * *